(12) United States Patent
Chien et al.

(10) Patent No.: US 10,617,719 B2
(45) Date of Patent: Apr. 14, 2020

(54) DEEP SEA WATER EXTRACT AND USE THEREOF

(71) Applicant: Taiwan DOW Biotech Co., Ltd., Taipei (TW)

(72) Inventors: Chiang-Ting Chien, Taipei (TW); Jyh-Chin Yang, Taipei (TW); Ping-Yi Huang, Ji'an Township, Hualien County (TW); Cheng-Huang Lin, Taipei (TW); Kwun-min Chen, Taipei (TW)

(73) Assignee: Taiwan Tian Shing Biotech Co., Ltd., New Taipei (TW)

( * ) Notice: Subject to any disclaimer, the term of this patent is extended or adjusted under 35 U.S.C. 154(b) by 142 days.

(21) Appl. No.: 15/099,206

(22) Filed: Apr. 14, 2016

(65) Prior Publication Data

US 2017/0042937 A1    Feb. 16, 2017

(30) Foreign Application Priority Data

Aug. 14, 2015 (TW) .............................. 104126596 A

(51) Int. Cl.
| | | |
|---|---|---|
| A61K 35/08 | (2015.01) | |
| A61K 9/00 | (2006.01) | |
| A61K 47/22 | (2006.01) | |
| A61K 33/00 | (2006.01) | |
| A61K 45/06 | (2006.01) | |
| A61K 31/352 | (2006.01) | |

(52) U.S. Cl.
CPC ............ *A61K 35/08* (2013.01); *A61K 9/0095* (2013.01); *A61K 31/352* (2013.01); *A61K 33/00* (2013.01); *A61K 45/06* (2013.01); *A61K 47/22* (2013.01)

(58) Field of Classification Search
CPC ...... A61K 35/08; A61K 9/0095; A61K 47/22; A61K 31/352; A61K 33/00; A61K 45/06
See application file for complete search history.

(56) References Cited

U.S. PATENT DOCUMENTS

2017/0042198 A1* 2/2017 Choung .................... A23L 2/38

FOREIGN PATENT DOCUMENTS

WO    WO 2015152615 A1 * 10/2015 ............... A23L 2/38

OTHER PUBLICATIONS

Chih-Ching Yang, "Deep-sea water containing selenium provides intestinal protection against duodenal ulcers through . . . ", Jul. 2014, PloS ONE 9(7), e96006.*
Hiroaki Takeuchi, "natural products and food components with anti-Helicobacter pylori activities", Jul. 2014, world journal of gastroenterology, vol. 20, issue 27, pp. 8971.*
Ha, B.G., KR 2014134580, 2014, Derwent Abstract, 3 pages. (Year: 2014).*

* cited by examiner

*Primary Examiner* — Sue X Liu
*Assistant Examiner* — Andriae M Holt
(74) *Attorney, Agent, or Firm* — Muncy, Geissler, Olds & Lowe, P.C.

(57) ABSTRACT

The present invention provides a deep sea water extract and a method for inhibiting the proliferation of *Helicobacter pylori* strains using the deep sea water extract, wherein the deep sea water extract has an organic component with a molecular weight of 685 to 690, 733 to 738 and 1,070 to 1,075. The deep sea water extract of the present invention can be applied in the prevention and treatment of *H. pylori* infection.

2 Claims, 24 Drawing Sheets

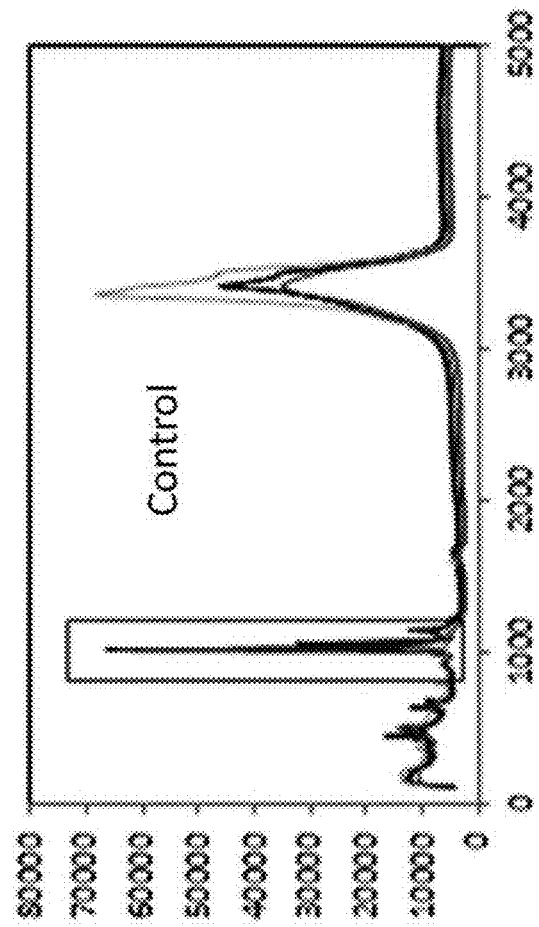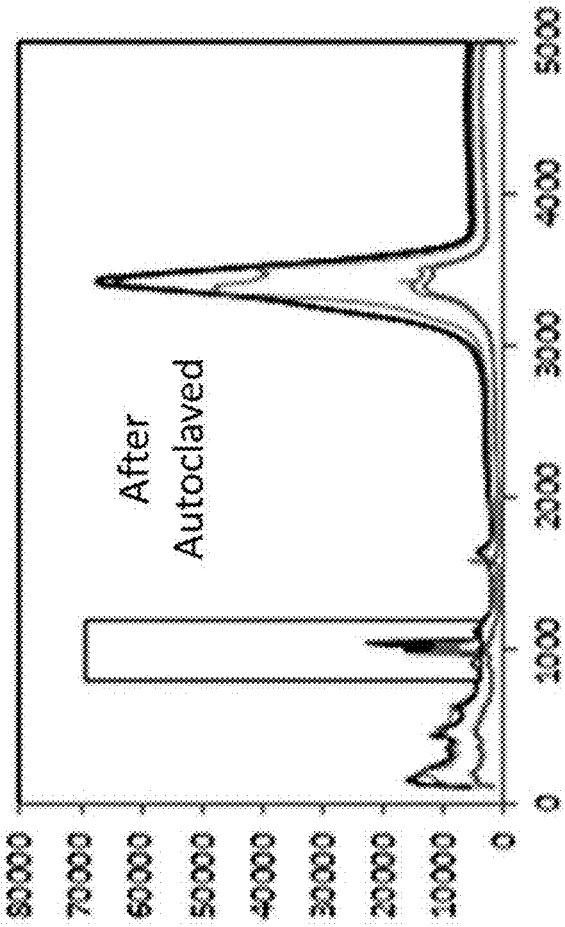
FIG. 4A
FIG. 4B

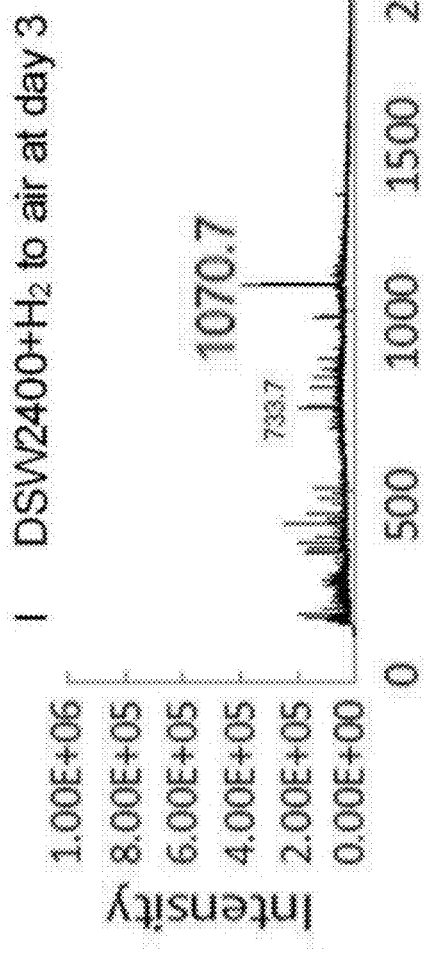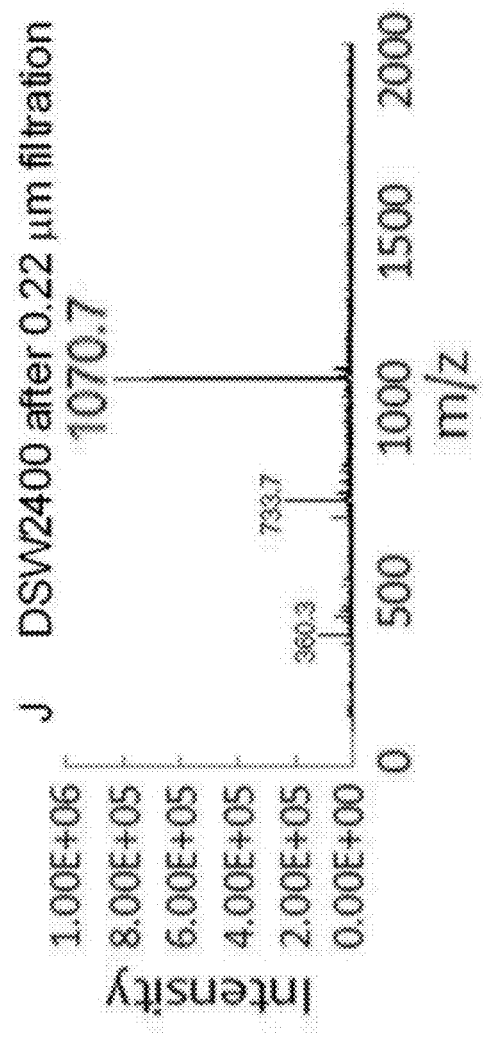
FIG. 5I
FIG. 5J

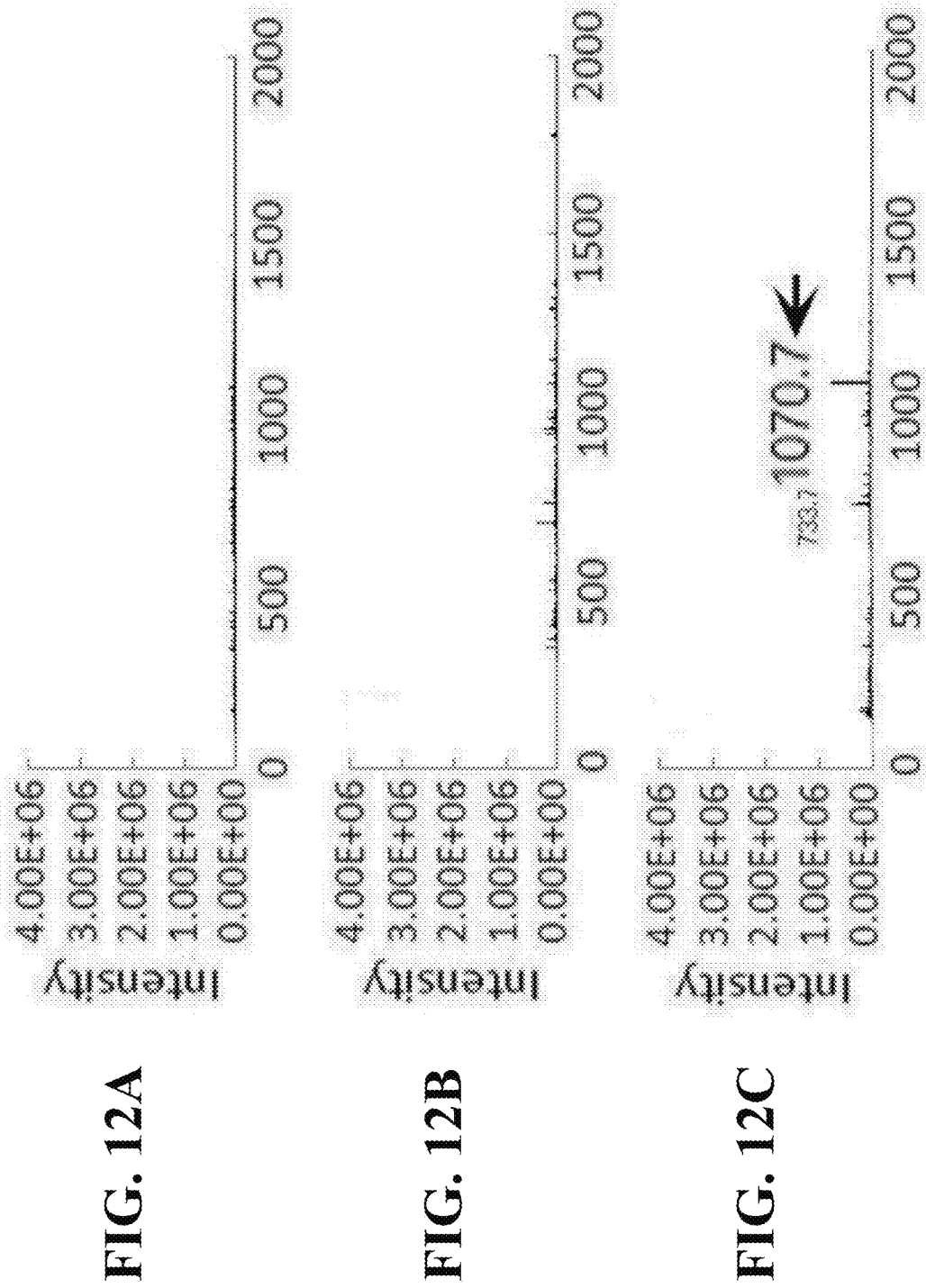

DEEP SEA WATER EXTRACT AND USE THEREOF

CROSS-REFERENCE TO RELATED APPLICATION

This application claims the priority of Taiwan patent application No. 104126596, filed on Aug. 14, 2015. The disclosure of which is incorporated herein by reference in its entirety

BACKGROUND OF THE INVENTION

1. Field of the Invention

The present invention relates generally to a method for inhibiting the proliferation of *Helicobacter pylori* strains using the deep sea water extract, and more particularly, to a method for inhibiting the proliferation of *Helicobacter pylori* using the deep sea water extract having an organic component.

2. The Prior Arts

A proton-pump inhibitor (PPI) and triple therapy have been the recommended treatment for *Helicobacter pylori* eradication for the past 10 years. Due to low compliance and steady increase in *Helicobacter pylori*, these treatments have become progressively less efficacious. After failure of first-line eradication treatment, second-line eradication including triple or quadruple therapy has been recommended, but these treatments still fail to overcome increasing drug-resistant strains. Therefore, it is an urgent requirement to provide a new component or composition for effective protection and treatment of *Helicobacter pylori* infection.

Currently, people have been known that a magnesium deficiency is closely associated with cardiovascular disease, the increase magnesium and calcium ion intake contribute to prevention of myocardial infarction. High magnesium intake may ameliorate high blood cholesterol and reduce the prevalence rates of metabolic syndrome and oxidative stress. Deep sea water (DSW) obtained from 200 m under the surface of the sea is characterized high magnesium, calcium and potassium ions, high nutrient or high organic components, low temperature and high purity. In recent years, DSW has been widely used in food processing industry, agriculture, pharmaceutical and cosmetic industries. The research has reported that DSW can reduce blood cholesterol and lipid peroxidation, prevent atherosclerosis and hypertension. In the development of atopic dermatitis, DSW ingestion or bathing improves dermatitis symptoms and allergic responses by reducing the inflammatory cell infiltration and inhibiting the upregulation of IgE, histamines and pro-inflammatory cytokines in the serum. DSW intake also has been shown to delay cataract developments.

Oxidative stress and inflammation are related to *H. pylori* infection and gastroduodenal ulcer, high magnesium intake can ameliorate *H. pylori* infection, gastric ulcer and gastroesophageal reflux disease and other symptoms. The administration of DSW can promote the anti-bacterial effects of *H. pylori* infection in human subjects, and *H. pylori* infection is closely related to gastritis, duodenal ulcer, gastric ulcer, gastric cancer and other stomach cancers, such as mucosal-associated lymphoid tissue lymphoma (MALToma). Limited documents show that DSW containing high concentration ions to inhibit the *H. pylori* growth in vitro study. And some reports show that serum magnesium concentration in human is associated with *H. pylori* colonized the stomach.

SUMMARY OF THE INVENTION

In the present invention, the anti-bacterial component of the deep sea water extract is validated by anti-*Helicobacter pylori* therapy, which administrates the patients with *H. pylori* infection with deep sea water extract for two week. The anti-bacterial effect is not induced by high magnesium, high calcium and high hardness water as well known; there are novel organic components in the deep sea water extract.

A objective of the present invention is to provide a method of inhibiting *Helicobacter pylori* infection, comprising administering an effective amount of a deep sea water extract to a subject in need thereof, wherein the deep sea water extract is obtained from a deep sea water by a manufacturing method, the manufacturing method is a combination of reverse osmosis (RO) and electrodialysis (ED), or a nanofiler method; and wherein the deep sea water extract is characterized to contain an organic component, and the organic component is selected from the group consisting of a molecular weight of 685 to 690, 733 to 738 and 1,070 to 1,075.

According to an embodiment of the present invention, the manufacturing method further comprises a method selected from the group consisting of gel filtration, dichloromethane (DCM) extraction, acetone extraction and chloroform extraction.

According to an embodiment of the present invention, the organic component has a preferable molecular weight of 1,070 to 1,075.

According to an embodiment of the present invention, the deep sea water is obtained at a depth greater than 200 m under the surface of the sea.

According to an embodiment of the present invention, the deep sea water extract further comprises an antioxidant to delay the degradation of the organic component, and the antioxidant is quercetin, (−)-epigallocatechin-3-gallate (EGCG) or $H_2$.

According to an embodiment of the present invention, the hardness of the deep sea water extract is 2,400 ppm to 4,800 ppm.

According to an embodiment of the present invention, the deep sea water extract is obtained from pasteurization or sterile filtration.

Another objective of the present invention is to provide a composition for the inhibition of *Helicobacter pylori* infection, consisting essentially of therapeutically effective amounts of deep sea water extract and an antioxidant, wherein the deep sea water extract contains an organic component which is selected from the group consisting of a molecular weight of 685 to 690, 733 to 738 and 1,070 to 1,075.

According to an embodiment of the present invention, the hardness of the deep sea water extract is 2,400 ppm to 4,800 ppm; the organic component has a preferable molecular weight of 1,070 to 1,075; the deep sea water extract is obtained at a depth greater than 200 m under the surface of the sea; and the antioxidant is quercetin, (−)-epigallocatechin-3-gallate (EGCG) or $H_2$.

BRIEF DESCRIPTION OF THE DRAWINGS

The present invention will be apparent to those skilled in the art by reading the following detailed description of a preferred embodiment thereof, with reference to the attached drawings, in which:

FIG. 4A is the spectrum of DSW 2400 treated with ED procedures using RENISHAW Raman spectrometer.

FIG. 4B is the spectrum of DSW 2400 treated with ED procedures and sterilized in an autoclave using RENISHAW Raman spectrometer.

FIG. 5I is the spectrum of 50 mL DSW 2400 of the present invention exposed to air for 3 days in the presence of $H_2$ (DSW 2400+ $H_2$ to air at day 3) using ESI/MS.

FIG. 5J is the spectrum of 50 mL DSW 2400 of the present invention filtered through a 0.22 μm filter membrane (DSW 2400 after 0.22 μm filtration) using ESI/MS.

FIG. 12A is the intensity value of the 1,070 component of RO water.

FIG. 12B is the intensity value of the 1,070 component of surface of the sea (SSW, which is obtained at depth of 50 m under the surface of the sea).

FIG. 12C is the intensity value of the 1,070 component of DSW 2400 sterilized in an autoclave.

DETAILED DESCRIPTION OF THE PREFERRED EMBODIMENT

Figures 1A, 1B, 1C:
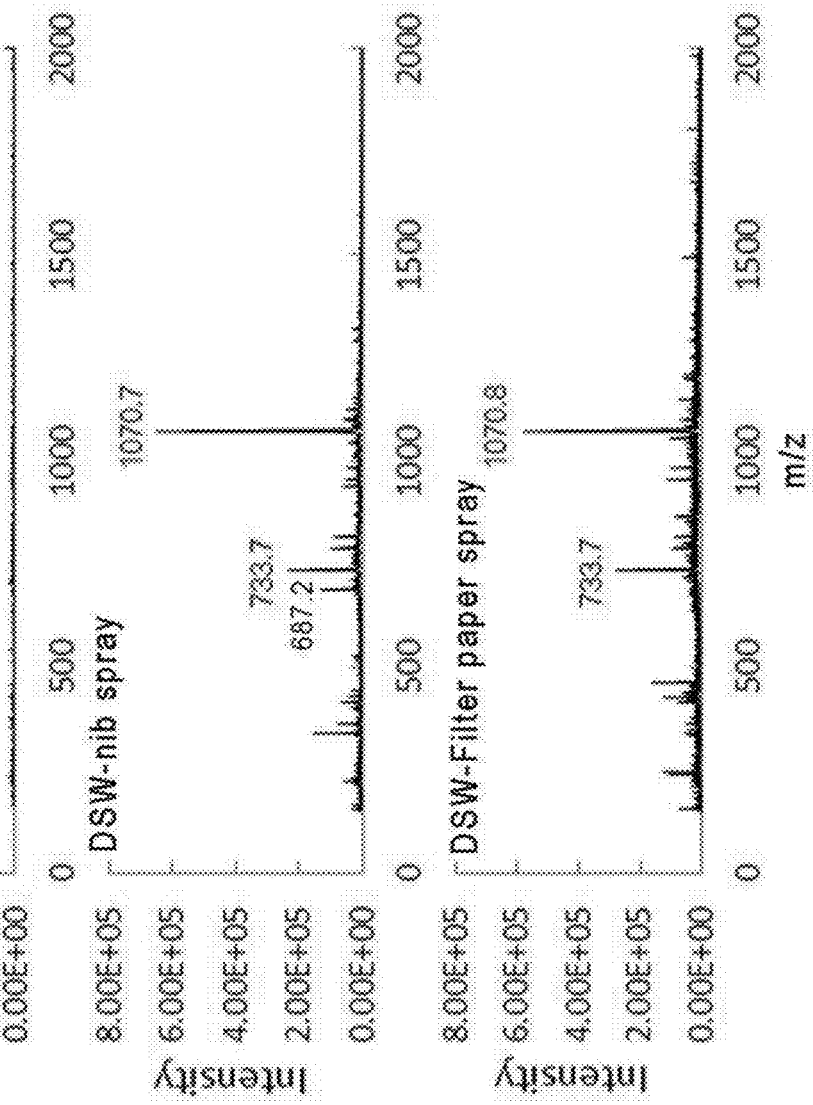
FIG. 1A is the mass spectrum of a hardness of 2,400 deep sea water extract (DSW 2400) using electrospray ionization mass spectrometry (ESI/MS); RO water detected by electrospray ionization using a bamboo pen nib (Nibs-MS) as a comparing group.
FIG. 1B is the mass spectrum of a hardness of 2,400 deep sea water extract (DSW 2400) using electrospray ionization mass spectrometry (ESI/MS); DSW 2400 of the present invention detected by Nibs-MS.
FIG. 1C is the mass spectrum of a hardness of 2,400 deep sea water extract (DSW 2400) using electrospray ionization mass spectrometry (ESI/MS); DSW 2400 of the present invention detected by electrospray ionization using a filter.

The accompanying drawings are included to provide a further understanding of the invention, and are incorporated in and constitute a part of this specification. The drawings illustrate embodiments of the invention and, together with the description, serve to explain the principles of the invention.

Definition

The "effective dosage" or "effective amount" represents the dosage of the banana flower extract that can inhibit prostate cell proliferation and the ability of synthesizing dihydrotestosterone stimulated by testosterone in the prostate cell. The appropriate effective amount may vary depending on the organism or individual treated but can be determined experimentally using various techniques, including a dose escalation study.

As used herein, the terms "active component", "antibacterial component", and "organic component" are interchangeable to refer to an organic component of any molecular weight.

As used herein, the data provided represent experimental values that can vary within a range of ±20%, preferably within ±10%, and most preferably within ±5%.

The purpose of present invention is to identify the components in the deep sea water extract having the antibacterial or other effects, and to provide a method of inhibiting *Helicobacter pylori* growth in a subject in need thereof. The present invention is to identify the organic components and its properties of the deep sea water obtained a depth greater than 200 m under the surface of the sea, and the activity of the organic components using Raman spectroscopy. The present invention validates that the active components of the deep sea water having ability of inhibiting *H. pylori* growth are not associated with high magnesium, calcium ions and high hardness.

EXAMPLE 1

Preparation of the Deep Sea Water (DSW) Extract

Deep sea water of the present invention is obtained at depth of greater than 200 m in Chisingtan Bay, Hua-Lien County, Taiwan and is permitted by Sone and Resource Industry Research and Development Center (Guanghuajian, Hualien, Taiwan). The modified DSW samples are prepared and provided by Sone and Resource Industry Research and Development Center (Guanghuajian, Hualien, Taiwan). The original DSW is processed by reverse osmosis (RO) and electrodialysis (ED) to lower hardness level, the hardness of DSW indicated in ppm is calculated by following formula:

$$[CaCO_3]\ ppm = ([Ca^{2+}] \times 2.5 + [Mg^{2+}] \times 4.1)\ ppm.$$

After RO and ED procedures, DSW drinking water with different hardness of 1,200 to 4,800 ppm is obtained. DSW drinking water is pasteurized at 80° C. for 60 s or used a sterile filtration and immediately stored at room temperature (25° C.) to obtain the deep sea water extract of the present invention.

The mineral contents in each sample of water are analyzed using an inductively coupled plasma optical emission spectrometer (JY ULTMA 2000, Horiba, France). The samples are included a hardness of 1,200 ppm DSW extract of the present invention (DSW 1200), a hardness of 2,400 ppm DSW extract of the present invention (DSW 2400) and a hardness of 2.1 ppm RO water. The pH value and major mineral concentrations of each sample are shown in Table 1. In addition, the present invention prepares the RO water, the deep sea water obtained at a depth greater than 200 m under the surface of the sea, the sea surface water obtained at a depth of 50 m under the surface of the sea (SSW) and other commercial deep sea water or sea surface water products to make comparison. The chemicals used, such as green tea (−)-epigallocatechin-3-gallate (EGCG) and quercetin, are purchased from Sigma-Aldrich Corporation.

Table 1 the pH value and major mineral concentrations of RO water, DSW 1200 and DSW 2400

|  | RO water | DSW1200 | DSW2400 |
| --- | --- | --- | --- |
| pH | 6.97 | 7.29 | 7.01 |
| Na (mg/L) | 17.0 | 390 | 778 |
| K (mg/L) | 0.47 | 3.34 | 6.68 |
| Ca (mg/L) | 6.31 | 50.2 | 100.5 |
| Mg (mg/L) | 0.76 | 285 | 570 |
| Ca/Mg | 8.30 | 0.18 | 0.18 |
| Hardness (ppm) | 18.9 | 1185 | 2588 |
| Sr (mg/L) | <0.1 | <0.1 | <0.1 |
| B (mg/L) | <0.1 | <0.1 | <0.1 |
| Fe (mg/L) | <0.05 | <0.05 | <0.05 |
| Zn (mg/L) | <0.05 | <0.05 | <0.05 |
| As (mg/L) | <0.05 | <0.05 | <0.05 |
| Cu (mg/L) | <0.05 | <0.05 | <0.05 |
| Mn (mg/L) | <0.05 | <0.05 | <0.05 |
| Cr (mg/L) | <0.05 | <0.05 | <0.05 |
| Mn (mg/L) | <0.05 | <0.05 | <0.05 |
| Ba (mg/L) | <0.05 | <0.05 | <0.05 |
| Ni (mg/L) | <0.05 | <0.05 | <0.05 |
| Cd (mg/L) | <0.05 | <0.05 | <0.05 |
| Pb (mg/L) | <0.05 | <0.05 | <0.05 |
| Hg (mg/L) | <0.05 | <0.05 | <0.05 |
| Cl (mg/L) | 1.74 | 1020 | 2040 |
| SO$_4$ (mg/L) | 4.91 | 600 | 1200 |

EXAMPLE 2

Electrospray Ionization Mass Spectrometry (ESI/MS)

The present invention detects the molecular weight of major components of the deep sea water extract using modified electrospray ionization method, nib-spray/ESI-MS (Nibs-MS). 3 μL sample solution is loaded onto the bamboo pen nib by dipping while methanol used as a volatile solvent (Harvard Apparatus Model 22), and the sample solution enters at speed 6 μL/min. When +3,000 v high voltage (Gamma, Fla., USA Model RR30-2R) is applied to the nib, the sample solution is rapidly ejected and ionized toward the mass inlet (Thermo Finnigan LCQ LC/MS), the limit of detection is 150-2,000 m/z, and rotary pumps (EDWARDS EM30) is used to maintain a vacuum in a mass spectrometer. After the detection completing, the bamboo pen nib is cleaned by ultrasonic cleaner (BRANSON 3510) for 30 min.

The electrospray ionization method is included three processes: nebulization, desolvation and ionization.

2.1 Nebulization: Forming Charged Droplets

When without applying a high voltage, an analyte solution pumped through outlet end of metal capillary forms the uniform distribution of droplets with positive ions and negative ions. When an analyte solution pumped through outlet end of metal capillary applying a high voltage, the strong electric field in the outlet end of metal capillary causes the positive and negative ions in the droplet generate a charge separation phenomenon. As applying positive voltage, the positive ions are repelled by the electromagnetic force toward the outlet end of metal capillary; the negative ions are attracted by positive electrical field toward the capillary wall. When the droplet accumulating in the outlet end, the accumulated positive charges at the surface of the droplet are destabilized, and finally the meniscus would be drawn out and deformed into a cone under the influenced of a very high electric filed. This is called a Taylor cone. As a result the size of the droplet decreases until it reaches the Rayleigh limit where the surface tension can no longer sustain the Coulomb force of repulsion. That is, the parent droplets disintegrate into much smaller offspring droplets, which is the process of forming charged droplets in electrospray ionization method.

2.2 Desolvation: Volatilization and Disintegration of Electrospray Droplet

The droplets with positive charge are released from the outlet end of metal capillary, and attracted to enter into the mass spectrometer due to a low electric filed at the mass analyzer's entrance. During the flight, the charged droplets are exposed to air evaporating the solvent in the droplet, the increasing charge density cases these droplets to further explode into even smaller droplets. When the droplets decrease in size to a certain extent, the repulsive forces between the like charges on the surface of the droplets exceed the forces of surface tension; the droplets disintegrate into smaller units for internal force balance. The degree of disintegration depends on the radius of the droplet, the surface tension of the solvent and the number of charges within the droplet. The same process repeats between electrospray and mass spectrometer, the charged droplets disintegrating and decreasing in size repeatedly causes the complete desolvation. In order to raise the efficiency of desolvation, high-volatile organic solvent is added to the analyte solution to lower surface tension for solvent volatilization during the electrospray, drying gas nebulization is also used to raise the efficiency of the electrospray, or applying airflow in the inlet end of the mass spectrometer toward electrospray is used to volatile solvent.

2.3 Ionization: Forming Gas-Phase Ion

So far people have no idea about the mechanism of the charged droplet forming gas-phase ions, but there are two theories accepted by scientists: M. Dole proposed the charged residue mechanism in 1968; Thomson, B. A. proposed the ion evaporation mechanism in 1976. The charged residue mechanism hypothesizes that as a droplet evaporates, its charge remains unchanged. The droplet's surface tension, ultimately unable to oppose the repulsive forces from the imposed charge, explodes into many smaller droplets. These Coulombic fissions occur until droplets containing a single analyte ion remain. When the solvent evaporates from the last droplet, a gas-phase ion forms. The ion evaporation mechanism hypothesizes that when droplets reach a certain radius (R=10-20 nm) through solvent evaporation and coulombic fission, resulting in the ion getting directly emitted from the droplet into the gas phase. This mechanism does not require evaporating the solvent from the last droplet to form gas-phase ion forms. In 1993 Fenn modified the ion evaporation mechanism to state the phenomenon of the large molecules with multiple charges. Fenn stated that the analytes remain neutral inside the neutral core of the charge droplet (charges lay on the surface). If the analyte is ntrinsically charged (e.g., proteins), this charged neutrality could be maintained either by a nearby counter anion as its "shadow" (i.e., ion pair formation) or by a proton transfer process between analyte and the solvent.

EXAMPLE 3

Raman Spectroscopy

Raman spectroscopy is a spectroscopic technique used to observe vibrational, rotational, and other low-frequency modes in a major component. Raman spectroscopy is commonly used in chemistry to provide a fingerprint by which molecules can be identified.

The Raman Effect occurs when electromagnetic radiation impinges on a molecule and interacts with the polarizable electron density and the bonds of the molecule in the phase (solid, liquid or gaseous) and environment in which the molecule finds itself. For the spontaneous Raman effect, which is a form of inelastic light scattering, a photon (electromagnetic radiation of a specific wavelength) excites (interacts with) the molecule in either the ground rovibronic state (lowest rotational and vibrational energy level of the ground electronic state) or an excited rovibronic state. This results in the molecule being in a so-called virtual energy state for a short period of time before an inelastically scattered photon results. The resulting inelastically scattered photon which is "emitted"/"scattered" can be of either lower (Stokes) or higher (anti-Stokes) energy than the incoming photon. In Raman scattering the resulting rovibronic state of the molecule is a different rotational or vibrational state than the one in which the molecule was originally, before interacting with the incoming photon (electromagnetic radiation). The difference in energy between the original rovibronic state and this resulting rovibronic state leads to a shift in the emitted photon's frequency away from the excitation wavelength. The Raman Effect is due to inelastic scattering and should not be confused with emission (fluorescence or phosphorescence) where a molecule in an excited electronic state emits a photon of energy and returns to the ground electronic state, in many cases to a vibrationally excited state on the ground electronic state potential energy surface.

EXAMPLE 4

Analyzing the Active Components of the Deep Sea Water Extract

The present invention analyzes the major components of a hardness of 2,400 ppm DSW extract of the present invention (DSW 2400) using electrospray ionization mass spectrometry (ESI/MS), which is included electrospray ionization using a bamboo pen nib (Nibs-MS), electrospray ionization using a filter and Raman spectroscopy.

Figure 1D:
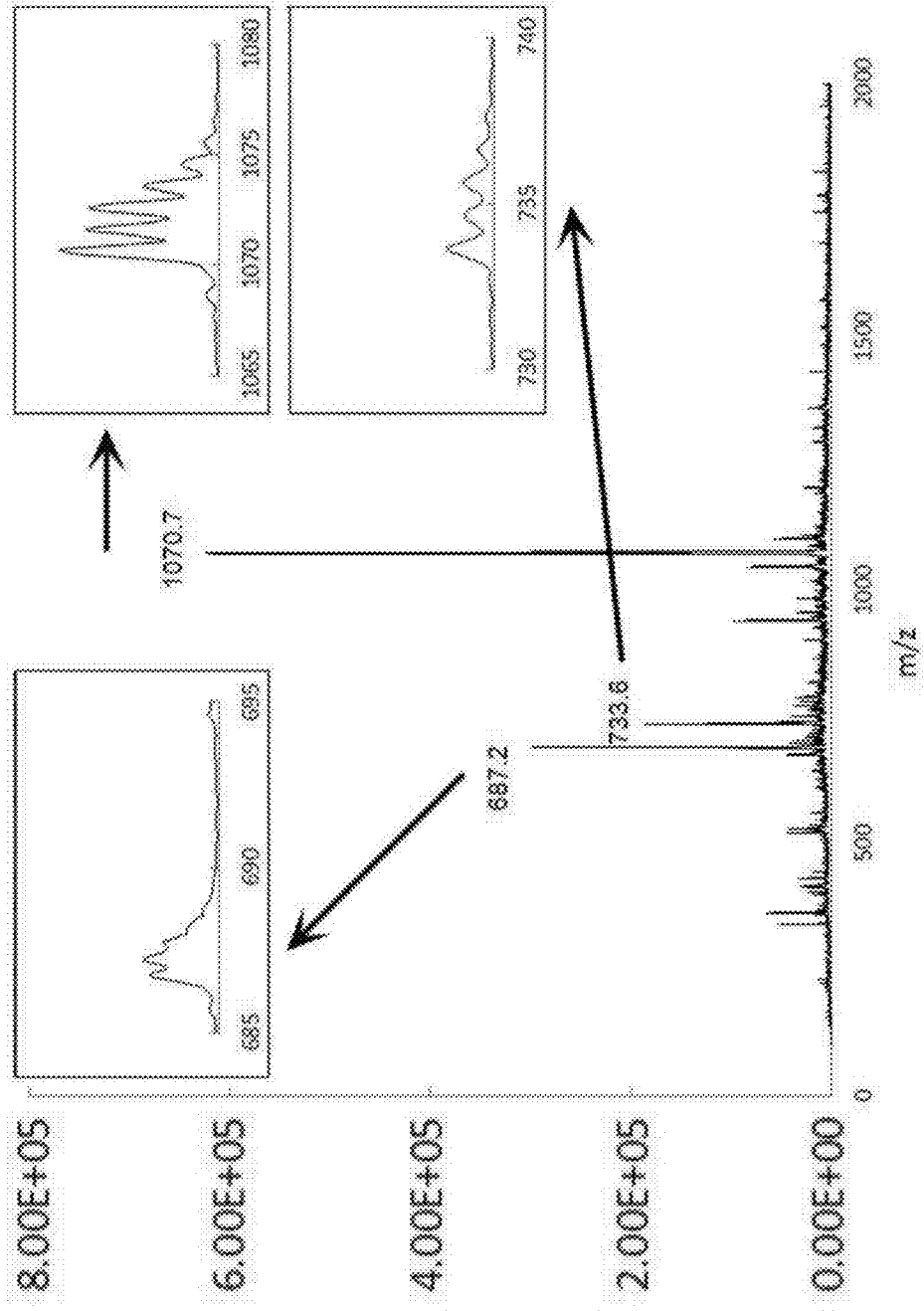
FIG. 1D is the mass spectrum of a hardness of 2,400 deep sea water extract (DSW 2400) using electrospray ionization mass spectrometry (ESI/MS); the enlarged view of DSW 2400 of the present invention detected by Nibs-MS.

The results of electrospray ionization mass spectrometry (ESI/MS) are shown in FIGS. 1A to 1D, three peak intensities of the major components in DSW 2400 are detected by Nibs-MS: the molecular weight of 687 (685-690), 733 (733-738) and 1,070 (1,070-1,075) (FIG. 1B); the mass spectrum of DSW 2400 shows the molecular weight of 687, 733, 1,070 (FIG. 1D). Also, two peak intensities of the major components in DSW 2400 are detected by electrospray ionization mass spectrometry using a filter (ESI/MS): 733 and 1,070 (FIG. 1C); and RO water is not detected any peak intensity by electrospray ionization mass spectrometry using Nibs-MS (FIG. 1A).

Figure 2:
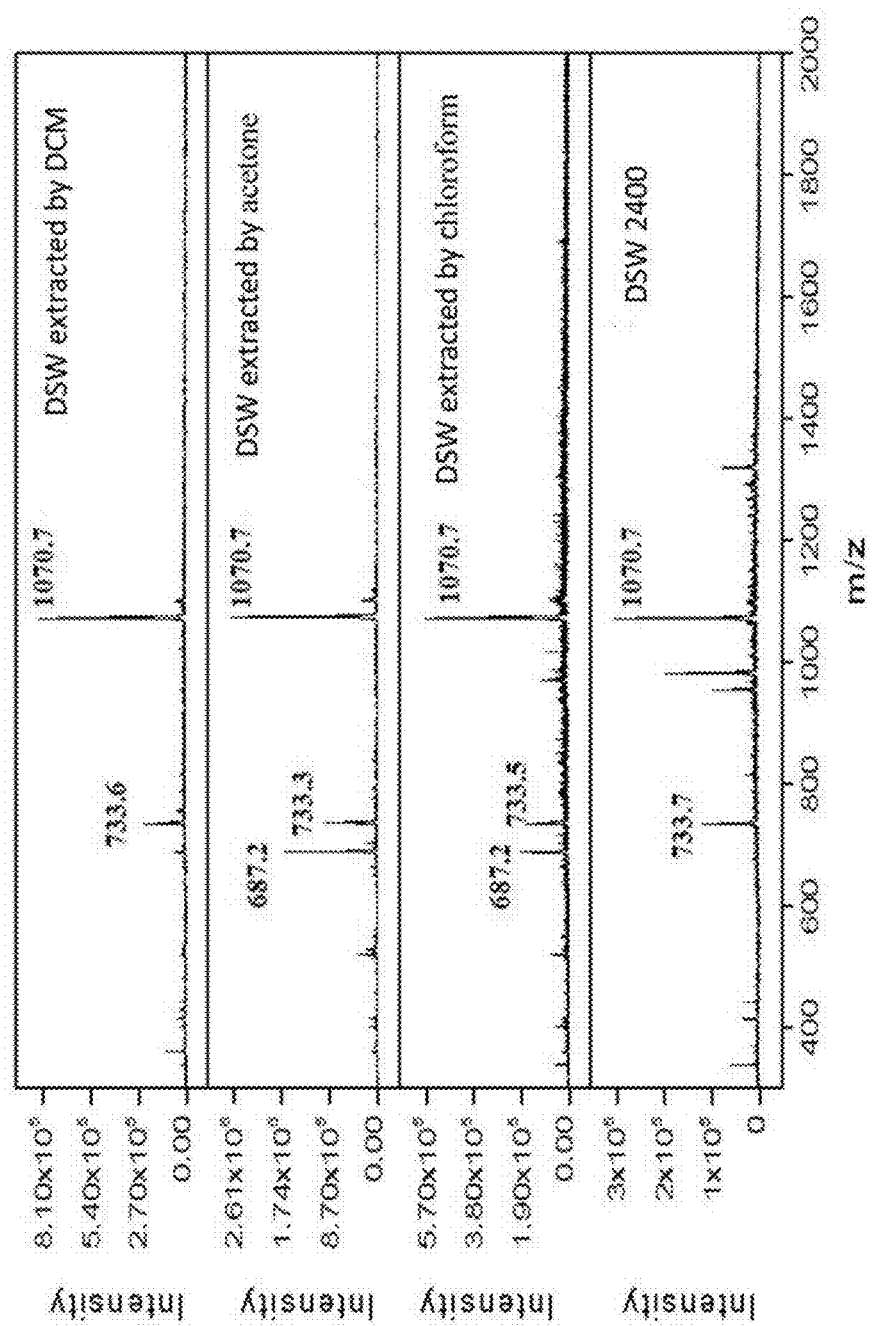
FIG. 2 is the mass spectrum of the DSW 2400 of the present invention extracted by dichloromethane (DCM), acetone, chloroform using ESI/MS.
Figures 3A, 3B, 3C:
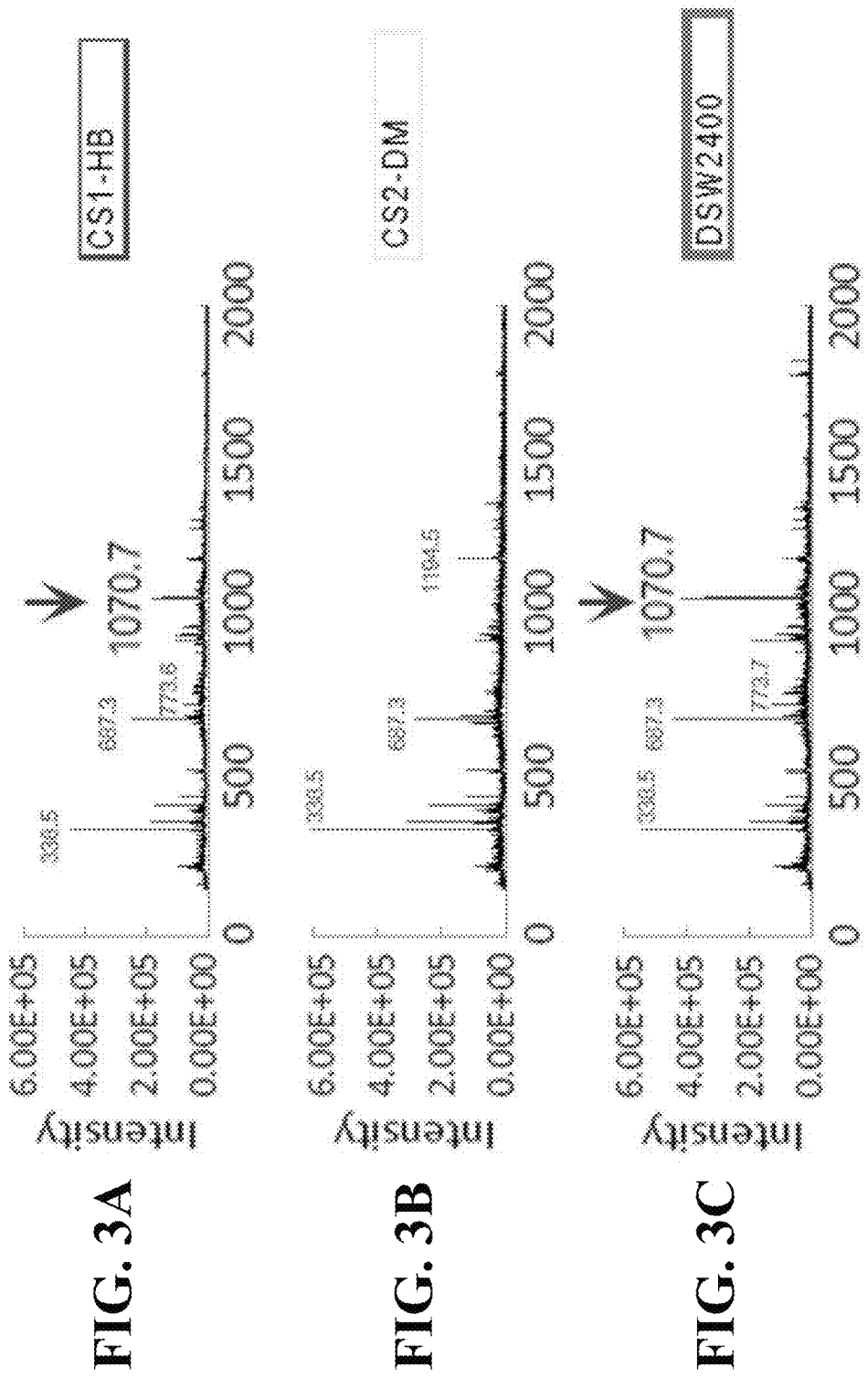
FIG. 3A is the mass spectrum of a commercial product of Taiwan fertilizer 1,400 deep sea water (CS1-HB) using ESI/MS.
FIG. 3B is the mass spectrum of a Deep Mine deep sea water (CS2-DM) using ESI/MS.
FIG. 3C is the mass spectrum of the DSW 2400 of the present invention (DSW 2400) using ESI/MS.
Figures 3D, 3E, 3F:
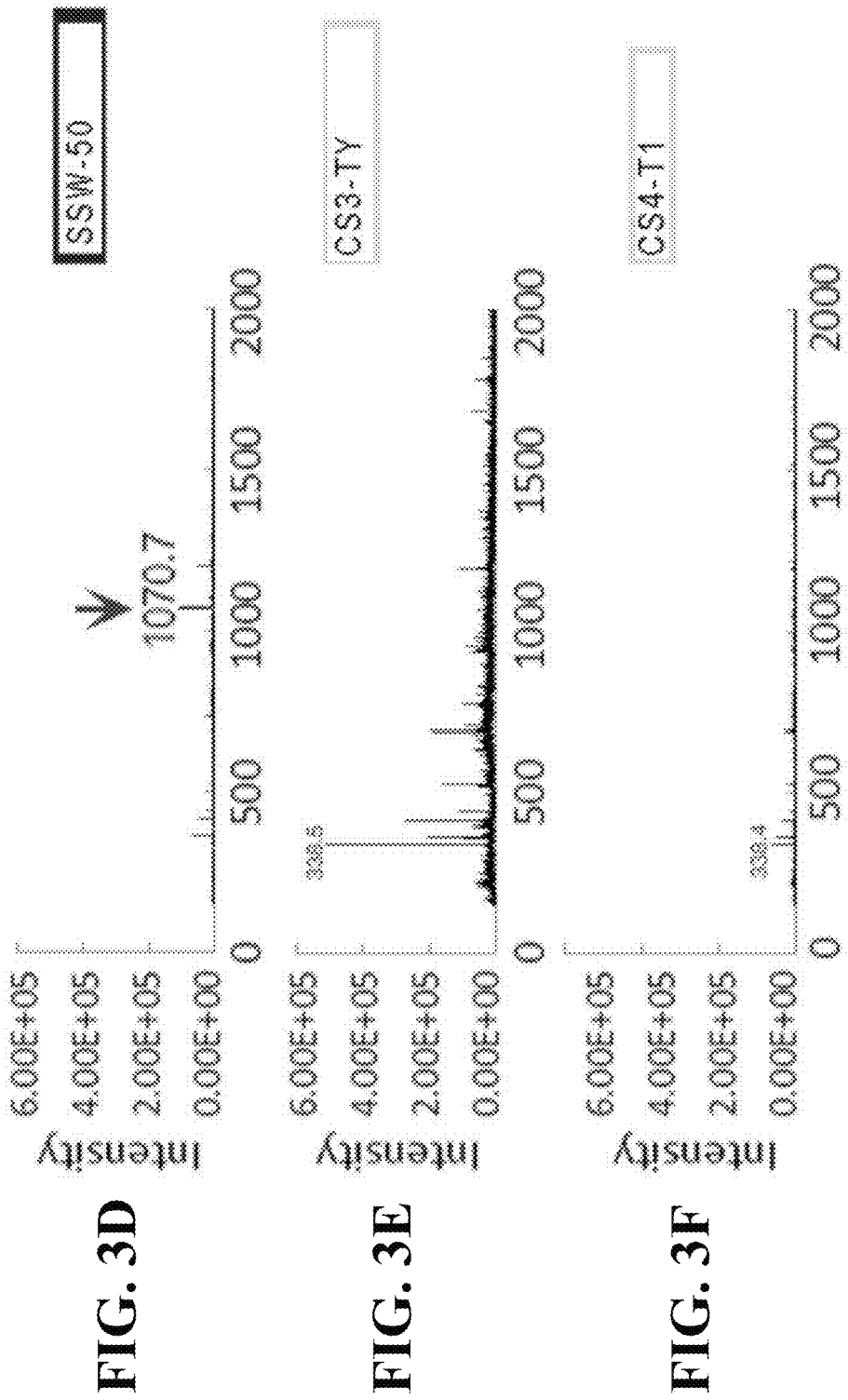
FIG. 3D is the mass spectrum of sea surface water (SSW-50) using ESI/MS.
FIG. 3E is the mass spectrum of a commercial product of Taiwan Salt sea alkaline ionized water (CS3-TY) using ESI/MS.
FIG. 3F is the mass spectrum of a commercial product of Uni-president pH 9.0 alkaline ionized water (CS4-T1) using ESI/MS.
Figures 3G, 3H:
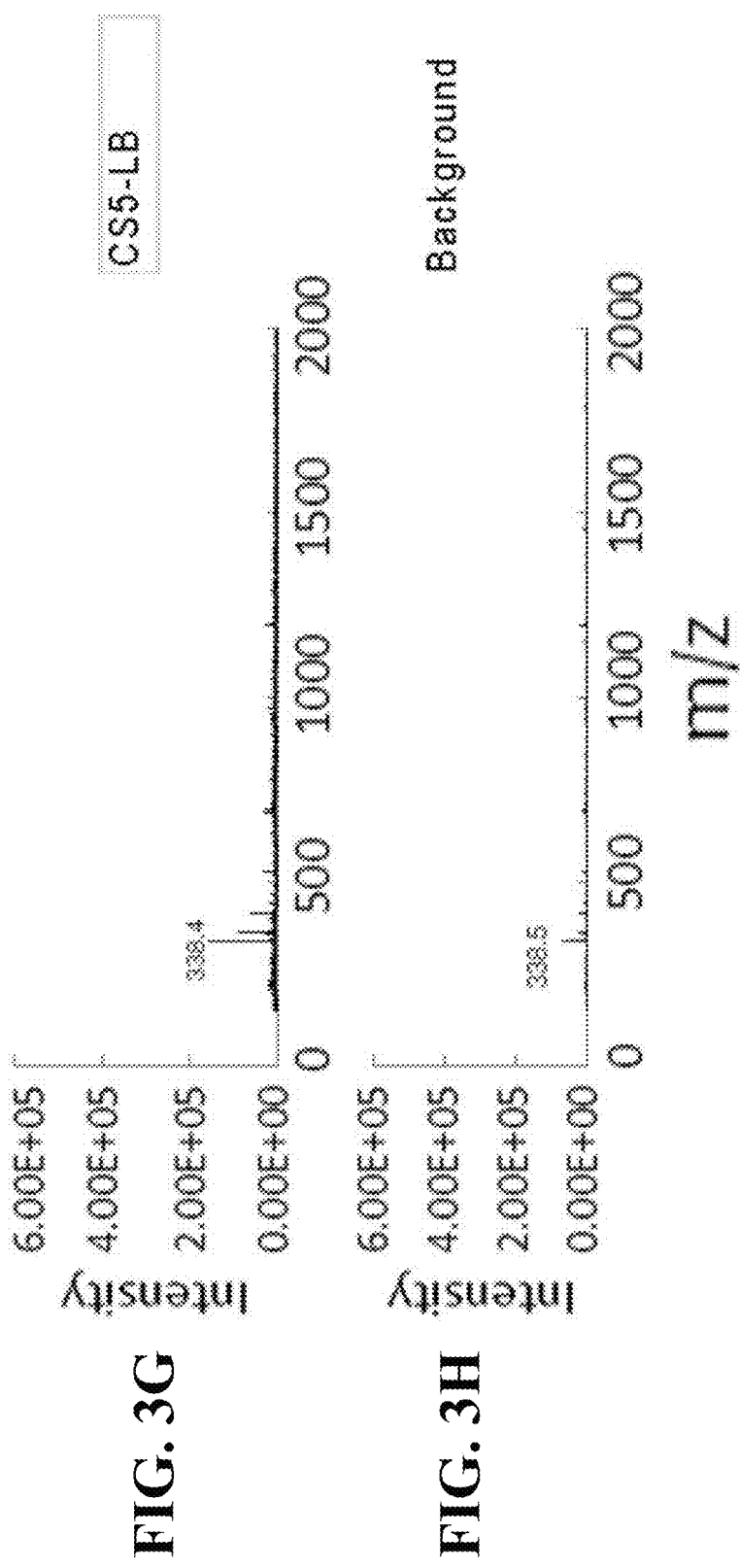
FIG. 3G is the mass spectrum of a commercial product of Light alkaline water (CS5-LB) using ESI/MS.
FIG. 3H is the mass spectrum of a background using ESI/MS; there is a background peak at 338.5.
Figure 5A:
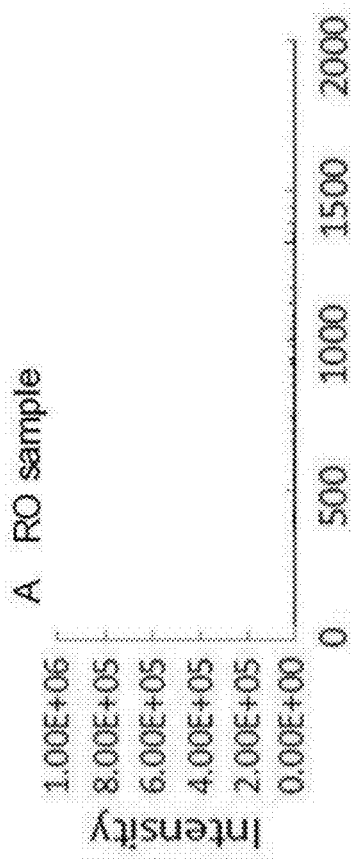
FIG. 5A is the spectrum of 50 mL reverse osmosis water after demineralizing by the reverse osmosis process (RO sample) using ESI/MS.
Figure 5B:
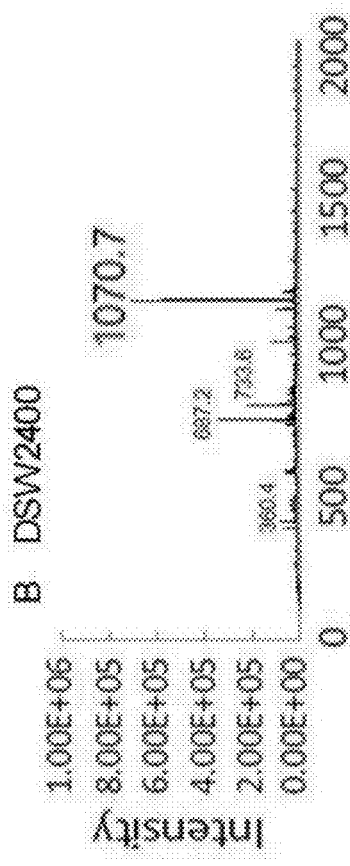
FIG. 5B is the spectrum of 50 mL DSW 2400 of the present invention without any treatment (DSW 2400) using ESI/MS.
Figure 5C:
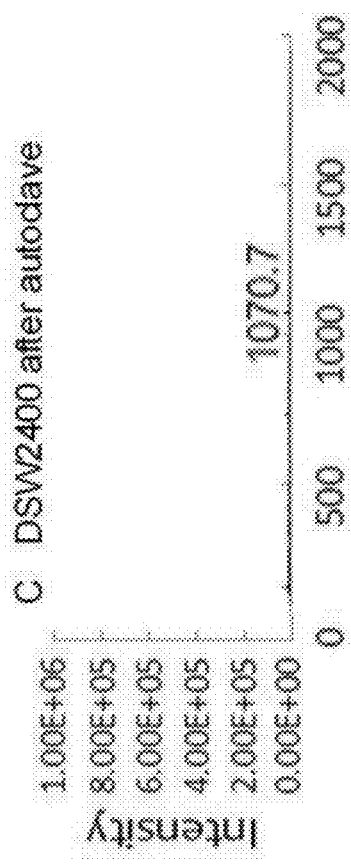
FIG. 5C is the spectrum of 50 mL DSW 2400 of the present invention sterilized in an autoclave for 15 minutes at 121° C. (DSW 2400 after autoclave) using ESI/MS.
Figure 5D:
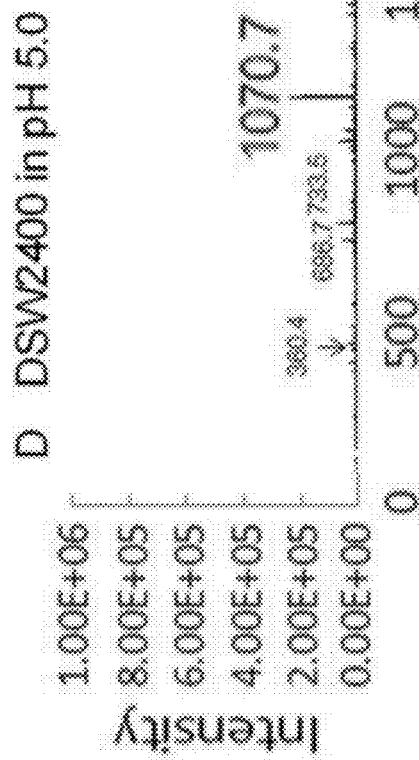
FIG. 5D is the spectrum of 50 mL DSW 2400 of the present invention at a pH of 5 under HCl treatment (DSW 2400 in pH 5.0) using ESI/MS.
Figure 5E:
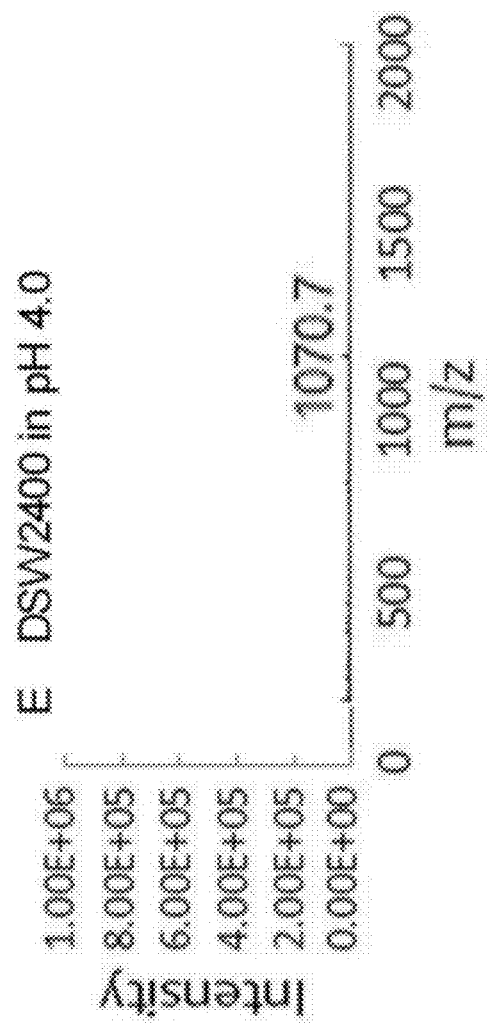
FIG. 5E is the spectrum of 50 mL DSW 2400 of the present invention at a pH of 4 under HCl treatment (DSW 2400 in pH 4.0) using ESI/MS.
Figure 5F:
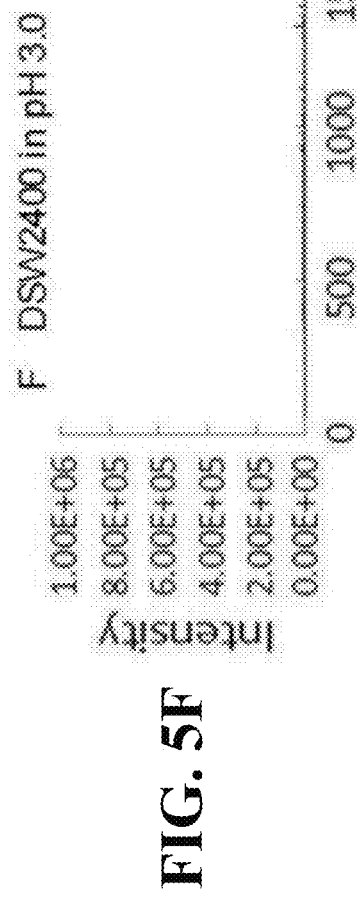
FIG. 5F is the spectrum of 50 mL DSW 2400 of the present invention at a pH of 3 under HCl treatment (DSW 2400 in pH 3.0) using ESI/MS.
Figure 5G:
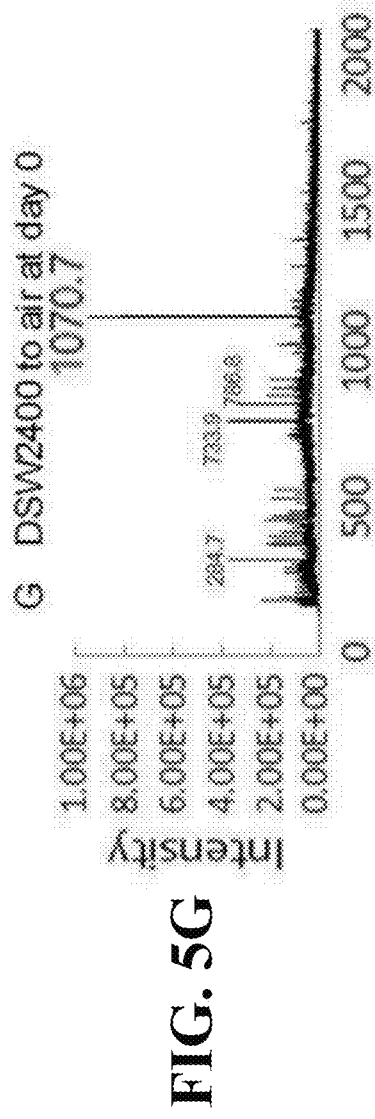
FIG. 5G is the spectrum of 50 mL DSW 2400 of the present invention exposed to air for a little bit (DSW 2400 to air at day 0) using ESI/MS.
Figure 5H:
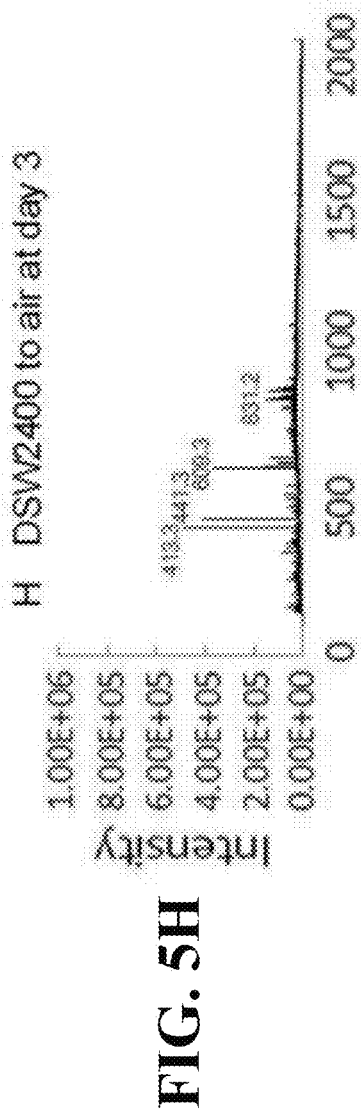
FIG. 5H is the spectrum of 50 mL DSW 2400 of the present invention exposed to air for 3 days (DSW 2400 to air at day 3) using ESI/MS.
Figure 6A:
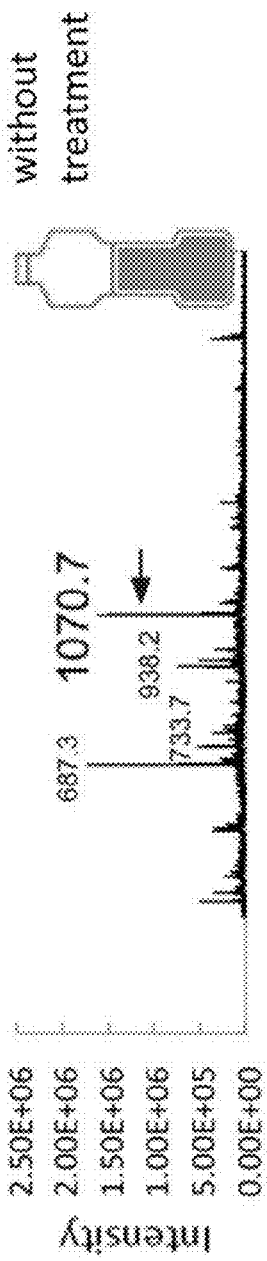
FIG. 6A shows 1,070 peak intensity of DSW 2400 without any treatments on the first day (Day 1) using ESI/MS.
Figure 6B:
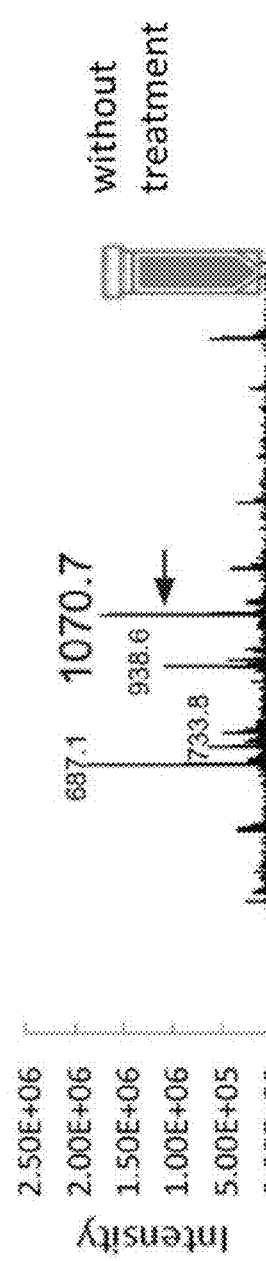
FIG. 6B shows 1,070 peak intensity of DSW 2400 of the present invention immediately analyzed after opening on the first day (Day 1) using ESI/MS.
Figure 6C:
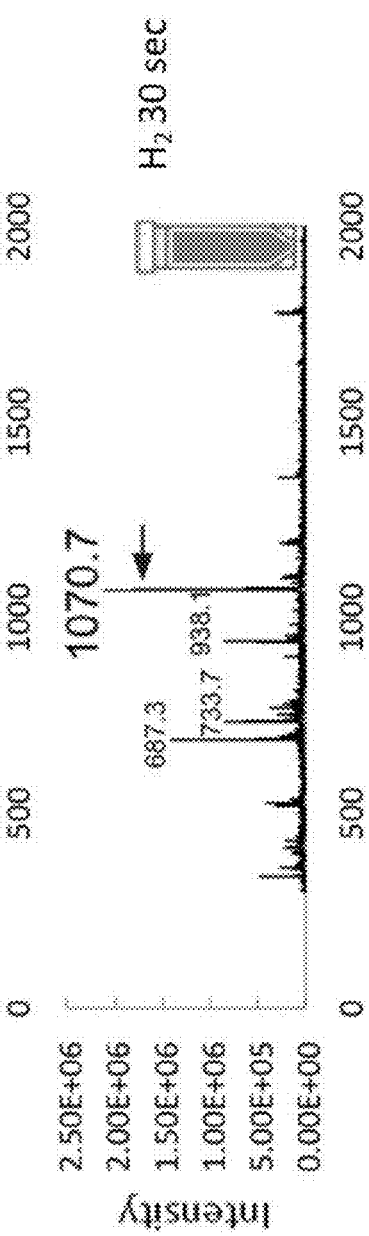
FIG. 6C shows 1,070 peak intensity of DSW 2400 of the present invention in the presence of $H_2$ for 30 sec on the first day (Day 1) using ESI/MS.
Figures 6D, 6E:
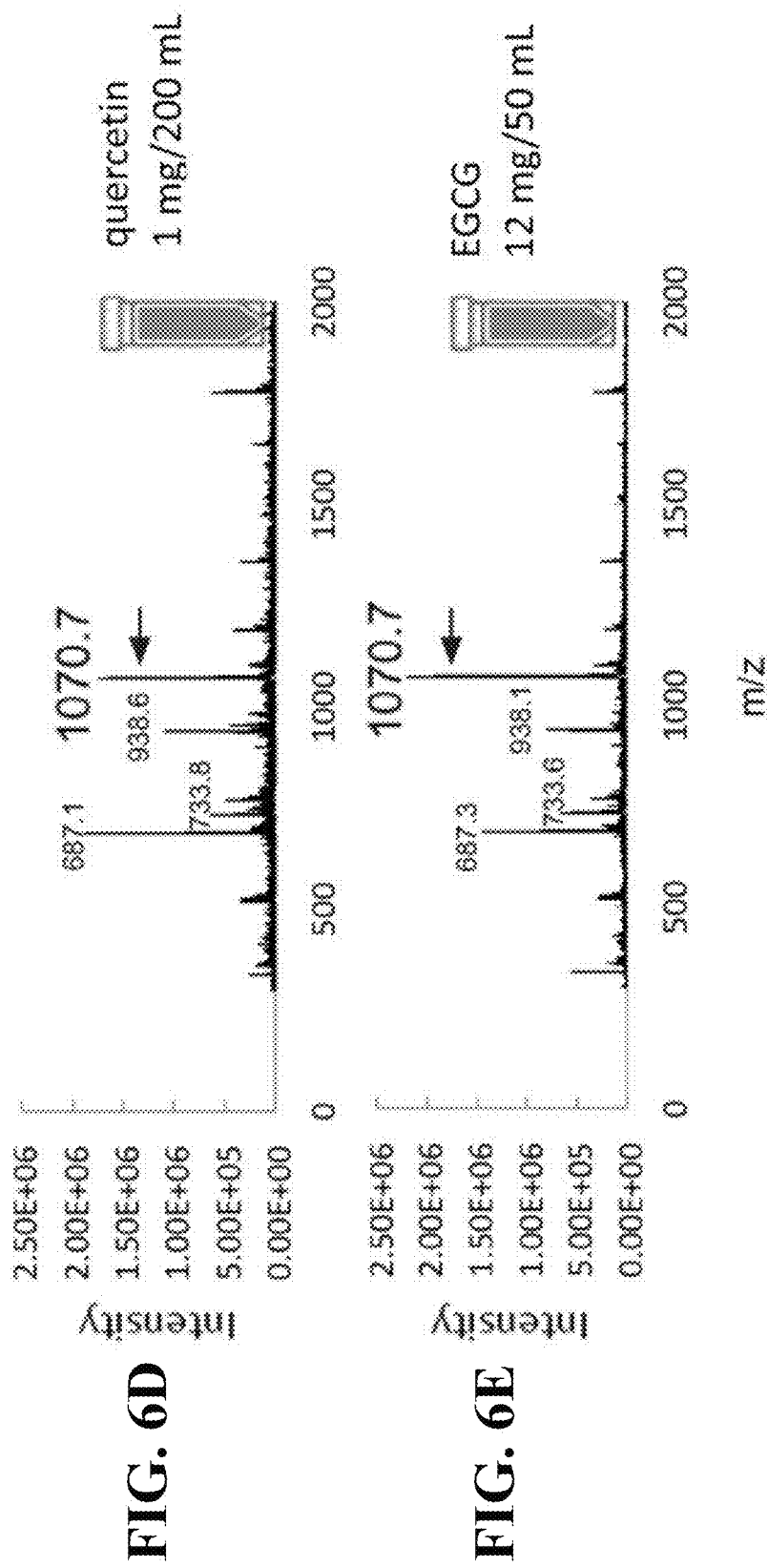
FIG. 6D shows 1,070 peak intensity of DSW 2400 of the present invention supplemented with 1 mg/200 mL quercetin on the first day (Day 1) using ESI/MS.
FIG. 6E shows 1,070 peak intensity of DSW 2400 of the present invention supplemented with 12 mg/50 mL green tea (−)-epigallocatechin-3-gallate (EGCG) on the first day (Day 1) using ESI/MS.
Figure 7A:
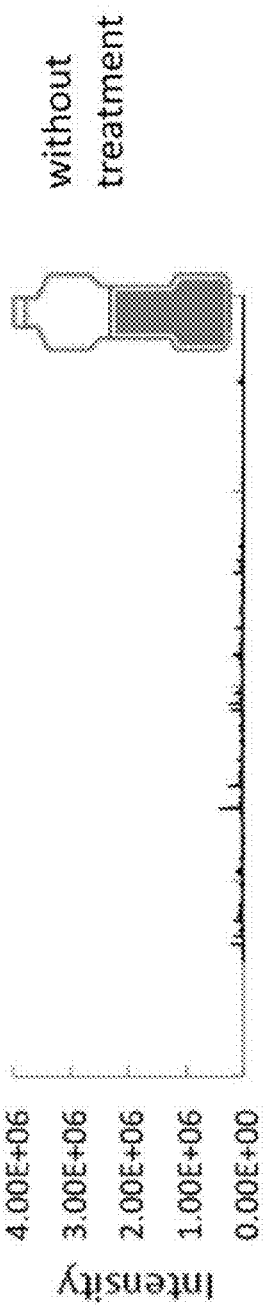
FIG. 7A shows 1,070 peak intensity of DSW 2400 without any treatments on the second day (Day 2) using ESI/MS.
Figure 7B:
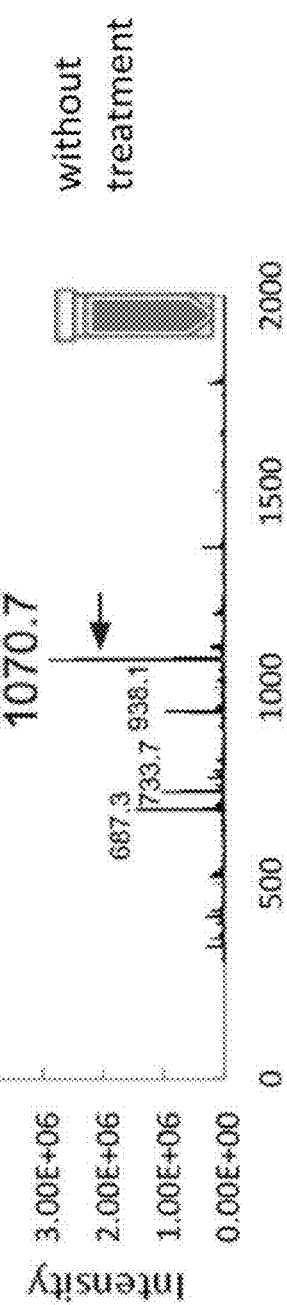
FIG. 7B shows 1,070 peak intensity of DSW 2400 of the present invention immediately analyzed after opening on the second day (Day 2) using ESI/MS.
Figure 7C:
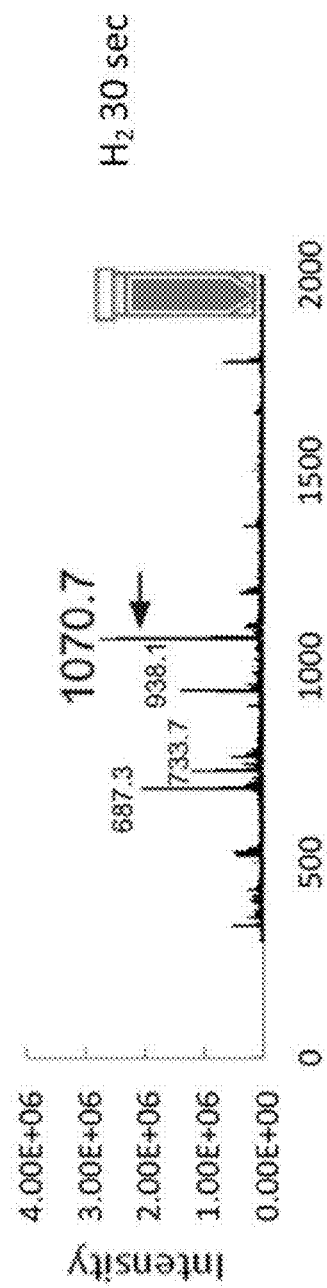
FIG. 7C shows 1,070 peak intensity of DSW 2400 of the present invention in the presence of $H_2$ for 30 sec on the second day (Day 2) using ESI/MS.
Figures 7D, 7E:
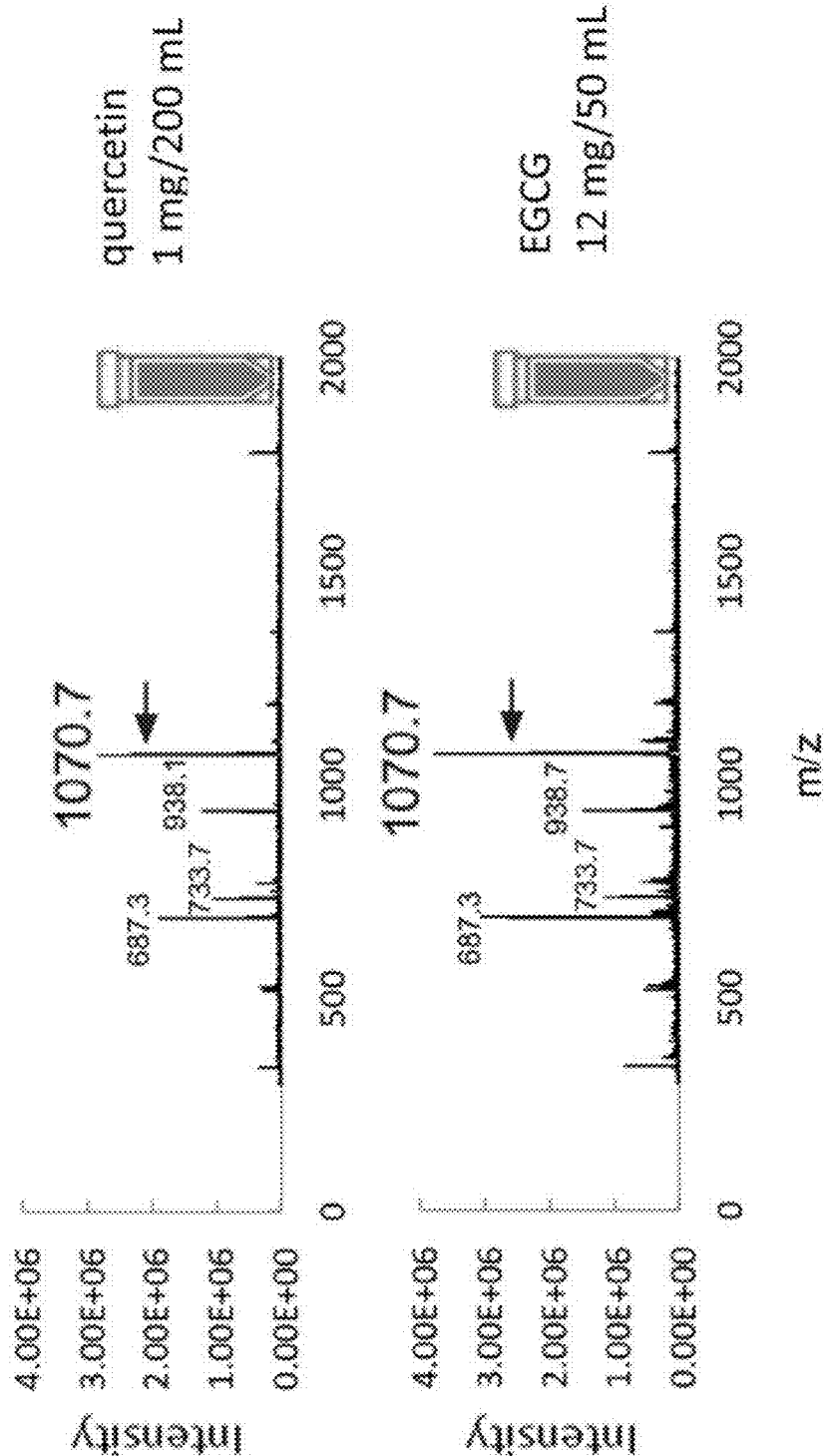
FIG. 7D shows 1,070 peak intensity of DSW 2400 of the present invention supplemented with 1 mg/200 mL quercetin on the second day (Day 2) using ESI/MS.
FIG. 7E shows 1,070 peak intensity of DSW 2400 of the present invention supplemented with 12 mg/50 mL green tea (−)-epigallocatechin-3-gallate (EGCG) on the second day (Day 2) using ESI/MS.
Figure 8A:
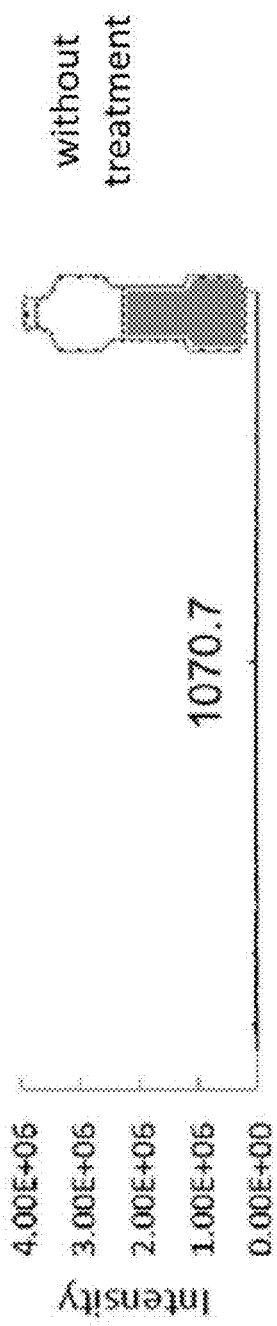
FIG. 8A shows 1,070 peak intensity of DSW 2400 without any treatments on the ninth day (Day 9) using ESI/MS.
Figure 8B:
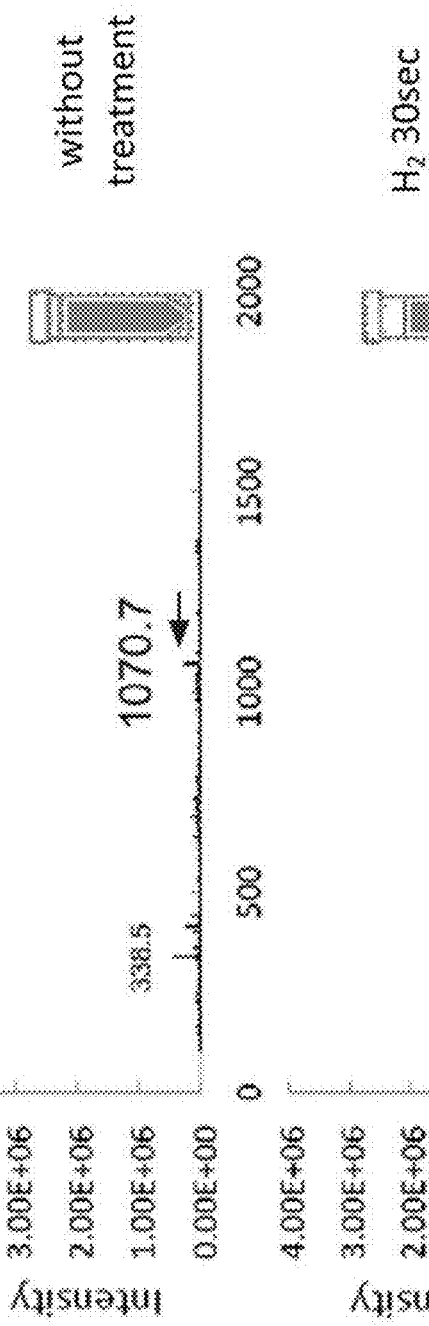
FIG. 8B shows 1,070 peak intensity of DSW 2400 of the present invention immediately analyzed after opening on the ninth day (Day 9) using ESI/MS.
Figure 8C:
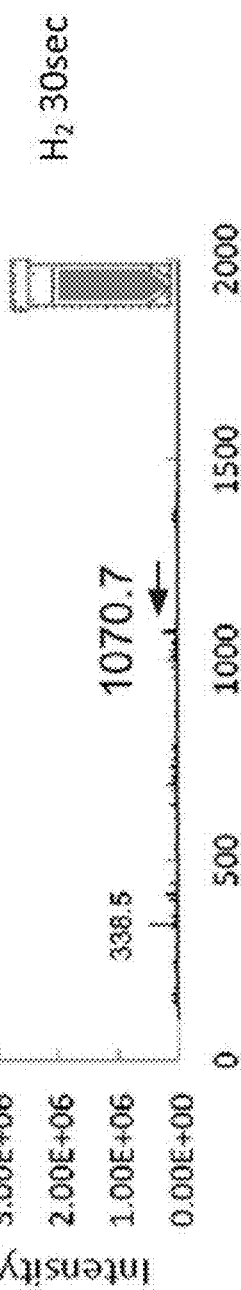
FIG. 8C shows 1,070 peak intensity of DSW 2400 of the present invention in the presence of $H_2$ for 30 sec on the ninth day (Day 9) using ESI/MS.
Figures 8D, 8E:
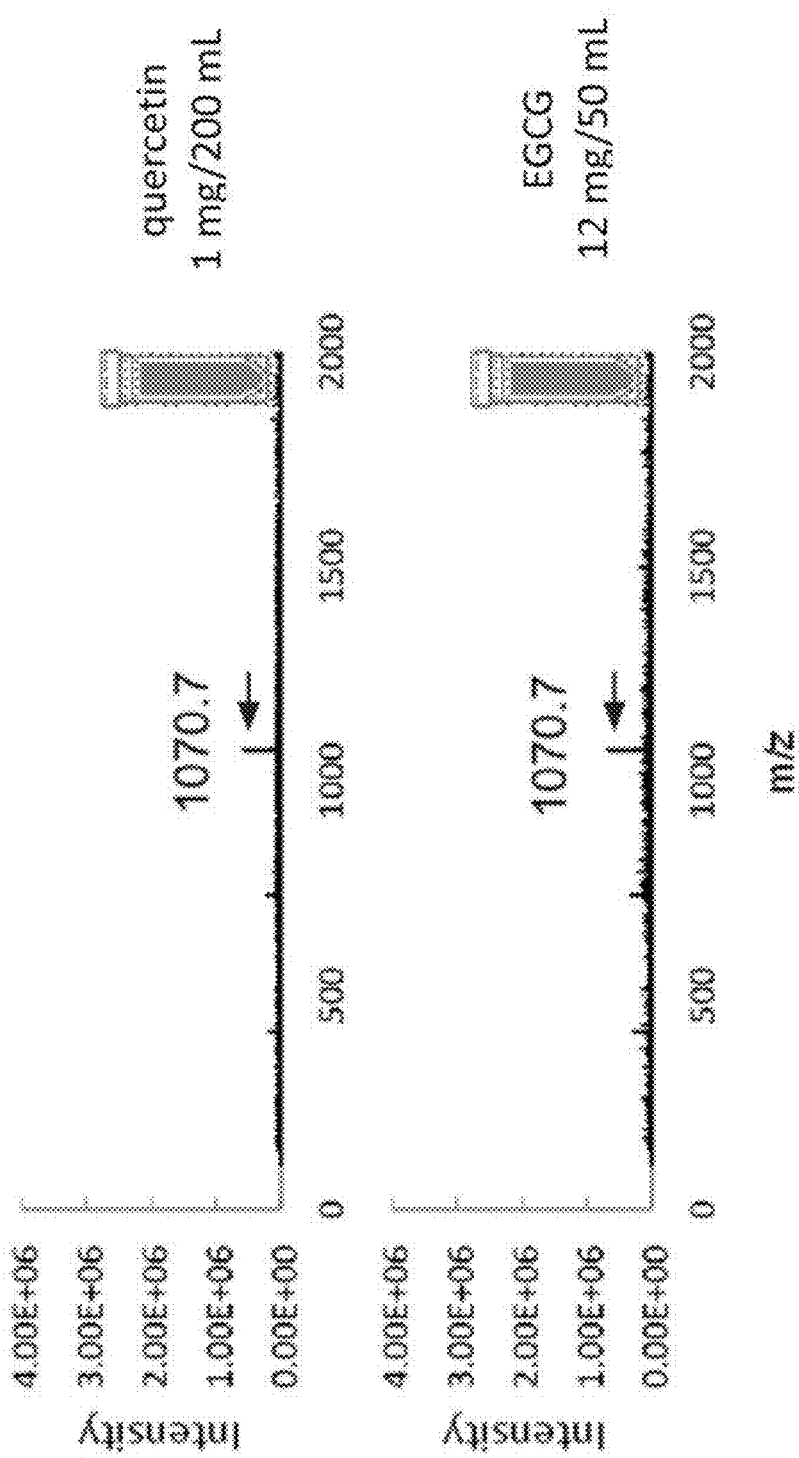
FIG. 8D shows 1,070 peak intensity of DSW 2400 of the present invention supplemented with 1 mg/200 mL quercetin on the ninth day (Day 9) using ESI/MS.
FIG. 8E shows 1,070 peak intensity of DSW 2400 of the present invention supplemented with 12 mg/50 mL green tea (−)-epigallocatechin-3-gallate (EGCG) on the ninth day (Day 9) using ESI/MS.

The present invention determines that water-soluble organic matter (DOM) of the deep sea water extract is organic components, the mass spectra of the deep sea water extract of the present invention extracted by three organic solution including dichloromethane (DCM), acetone, chloroform is compared to the mass spectrum of DSW 2400. As shown in FIG. 2, the mass spectra of the deep sea water extract extracted by DCM, acetone, chloroform using Nibs-MS show the molecular weight of 687, 733, and 1,070. And the mass spectrum of DSW 2400 detected by electrospray ionization mass spectrometry using a filter (ESI/MS) shows the molecular weight of 733 and 1,070. Therefore, these results validate that the components having the molecular weight of 687, 733, 1,070 of the deep sea water extract are organic components.

The present invention analyzes the seawater from other area, seawater treated with different process or sea surface water (SSW) using ESI/MS, as shown in FIGS. 3A to 3H, the components having a molecular weight below 2,000 show different molecular weight, the mass spectrum of DSW2400 shows higher peak intensity at 1,070 than sea surface water (SSW-50) and a commercial product of Taiwan fertilizer 1400 deep sea water (CS1-HB). The mass spectra of a commercial product of Deep Mine deep sea water (CS2-DM), a commercial product of Taiwan Salt sea alkaline ionized water (CS3-TY), a commercial product of Uni-president pH 9.0 alkaline ionized water (CS4-T1) and a commercial product of Light alkaline water CS5-LB do not show 1,070 peak, which indicates that above-mentioned products do not contain the organic component.

The present invention analyzes DSW 2400 treated with ED procedures using commercial RENISHAW Raman spectrometer. As shown in FIGS. 4A and 4B, the intensity of the deep sea water extract sterilized in an autoclave for a 1,000 $cm^{-1}$ (wavenumber region) molecular vibration (FIG. 4B) is significantly reduced than the deep sea water extract without sterilizing in an autoclave (FIG. 4A), which indicates that the organic components would be destroyed by heating.

EXAMPLE 5

The Properties of the Deep Sea Water Extract Affected by Acid 400 mL a hardness of 2,400 ppm DSW extract of the present invention (DSW 2400) immediately is analyzed after opening. Ten solutions are added into each tube respectively, which comprising: (A) 50 mL reverse osmosis (RO) water after demineralizing by the reverse osmosis process; (B) 50 mL DSW 2400 of the present invention without treatment; (C) 50 mL DSW 2400 of the present invention in the tube, autoclave for 15 minutes at 121° C.; (D) 50 mL DSW 2400 of the present invention at a pH of 5 under HCl treatment for electrodialysis processing; (E) 50 mL DSW 2400 of the present invention at a pH of 4 under HCl treatment for electrodialysis processing; (F) 50 mL DSW 2400 of the present invention at a pH of 3 under HCl treatment for electrodialysis processing; (G) 50 mL DSW 2400 of the present invention exposed to air for a little bit; (H) 50 mL DSW 2400 of the present invention for 3 day for electrodialysis processing; (I) 50 mL DSW 2400 of the present invention in the presence of $H_2$ for electrodialysis processing; (J) 50 mL DSW 2400 of the present invention filtered through a 0.22 μm filter membrane for electrodialysis processing. These ten samples are detected by electrospray ionization mass spectrometry (ESI/MS), as shown in FIGS. 5A to 5J, the 1,070 peak in each sample shows different intensity, the 1,070 peaks of DSW 2400 of the present invention exposed to air for a little bit and DSW 2400 of the present invention filtered through a 0.22 μm filter membrane show more high intensity signals as compared to others. DSW 2400 of the present invention at a pH of 3 to 4 under HCl treatment, DSW 2400 of the present invention exposed to air for a long time and sterilized in an autoclave show the 1,070 peak of the organic component destroyed.

EXAMPLE 6

The Preservation of the Deep Sea Water Extract Affected by Antioxidants 400 mL 2,400 ppm DSW extract of the present invention (DSW 2400) immediately is analyzed after opening (Day 1) by electrospray ionization mass spectrometry (ESI/MS). Fill beaker with 200 mL 2,400 ppm DSW extract to dispense 50 mL of 2,400 ppm DSW extract into each of 4 tubes, and then close the cap of tube tightly after treatment. 2,400 ppm DSW extract in the first tube is without treatment (reducing exposure to air); 2,400 ppm DSW extract in the second tube is treated in the presence of $H_2$ for 30 sec (may cause overflow); 2,400 ppm DSW extract in the third tube is treated by adding antioxidants (quercetin) (1 mg/200 mL) and 2,400 ppm DSW extract in the fourth tube is treated by adding antioxidants (green tea (−)-epigallocatechin-3-gallate; EGCG) (12 mg/50 mL); the residue of 200 mL 2,400 ppm DSW extract is exposure to air in original container as a without treatment control group. All samples with different treatment are opened to detect the 1,070 peak intensity using electrospray ionization mass spectrometry (ESI/MS) on the second and ninth day.

As shown in FIGS. 6A to 6E, 7A to 6E and 8A to 8E, the 1,070 peak of each sample after treatment on the first day show similar peak intensity detected by ESI/MS (FIGS. 6A to 6E). The 1,070 peaks after treatment on the second day show unchanged in the groups of reducing exposure to air, treating in the presence of $H_2$ for 30 sec and supplemented with antioxidants (quercetin or EGCG), compared to the without treatment control group which not show 1,070 peak (FIGS. 7A to 7E). The 1,070 peaks after treatment on the ninth day show significantly reducing peak intensity in the all groups detected by ESI/MS, but the group of supplemented with antioxidants (quercetin or EGCG) shows more higher intensity than other groups (FIGS. 8A to 8E).

Figure 9:
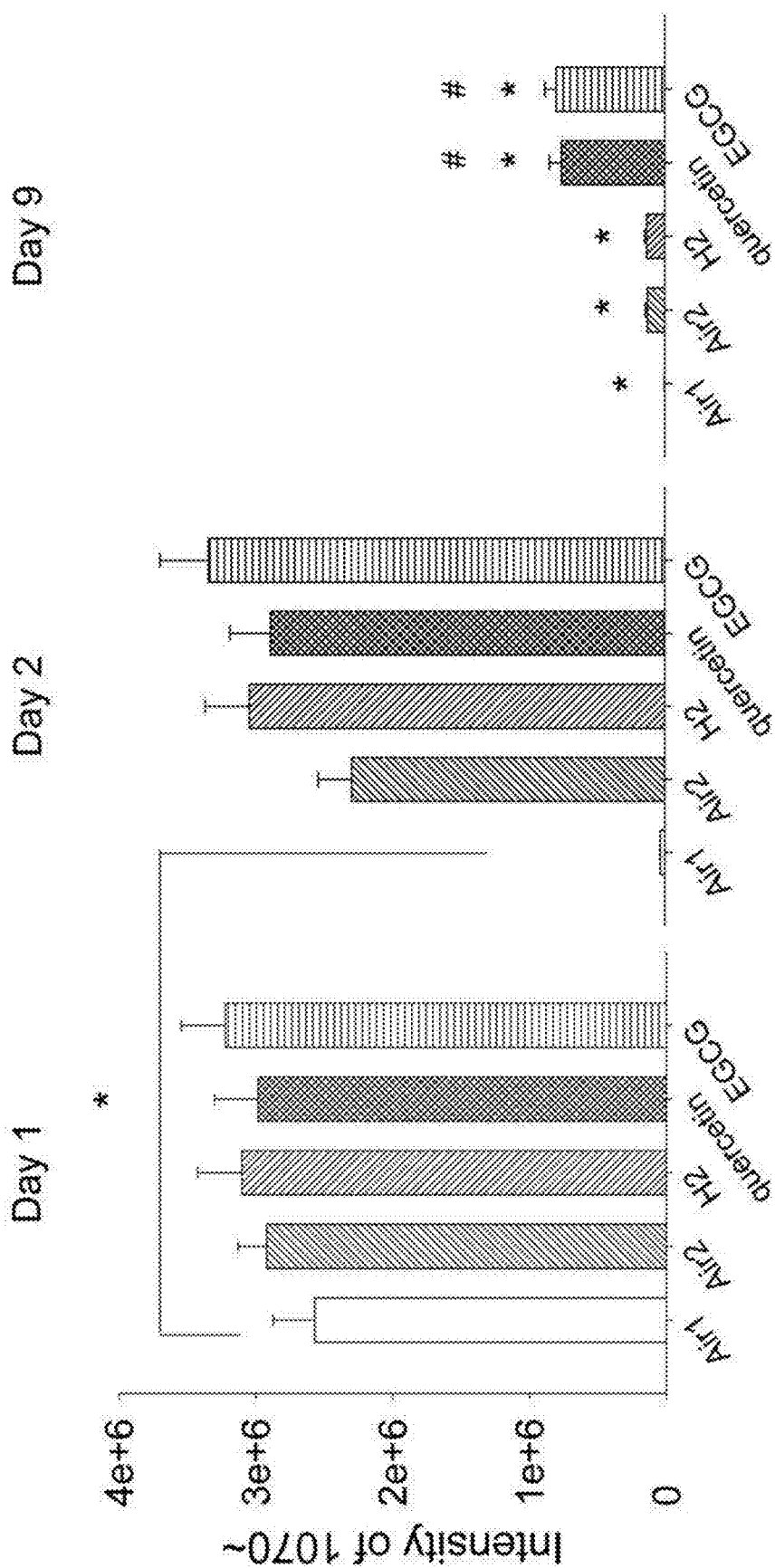
FIG. 9 is bar chart to analyze 1,070 peak intensity through different treatments detected by ESI/MS on the first day (Day 1), the second day (Day 2) and the ninth day (Day 9). The experiment was run in triplicate. *P<0.05 compared with individual control group on the first day; # P<0.05 compared with the without treatment group (Air 2) on the ninth day.

In the present invention, bar chart is used to compare 1,070 peak intensity through different treatments detected by ESI/MS on the first day (Day 1), the second day (Day 2) and the ninth day (Day 9). As shown in FIG. 9, 1,070 peak intensity in each group is still hold on second day except the group of the without treatment control group (labeled as Air 1). 1,070 peak intensity in each group is significantly reduced on the ninth day, but the groups of adding antioxidants, such as $H_2$, quercetin or EGCG, show higher 1,070 peak intensity. The without treatment control group is 200 mL 2,400 ppm DSW extract is exposure to air (Air 1); the without treatment group is 50 mL 2,400 ppm DSW extract to close 50 mL-tube tightly (labeled as Air 2); the treatment with $H_2$ group is 2,400 ppm DSW extract in the presence of $H_2$ for 30 sec to close into 50 mL-tube tightly (labeled as $H_2$); the treatment with quercetin group is 50 mL 2,400 ppm DSW extract added into 50-mL tube supplemented with 1 mg/200 mL quercetin to close tightly (labeled as quercetin); the treatment with EGCG group is 50 mL 2,400 ppm DSW extract added into 50-mL tube supplemented with 12 mg/50 mL EGCG to close tightly (labeled as EGCG). These results show the organic component of the DSW extract cause oxidant damage due to exposure to air, but adding safe and edible antioxidants can exhibit reduced oxidant generation of 1,070 organic component.

The DSW extract is processed reverse osmosis (RO) and electrodialysis or other method such as nanofiler to obtain or retain the active components having the ability of inhibiting *Helicobacter pylori* growth. The DSW extract are further processed gel filtration, extracted by dichloromethane (DCM), acetone or chloroform to obtain the active components with molecular weight below 2,000 having the ability of inhibiting *Helicobacter pylori* growth. The active components are detected by ESI/MS, which shows the peak intensities at the molecular weight of 687 (685-690), 733 (733-738) and 1,070 (1,070-1,075). DSW 2400 of the present invention extracted by DCM, acetone, chloroform detected by ESI/MS shows the peak intensity at the molecular weight of 687, 733 and 1,070, which validates that the active components with the molecular weight of 687, 733 and 1,070 are organic components.

The organic components with the molecular weight of 687, 733 and 1,070 of DSW extract are destroyed by exposure to air, heating up to 121° C. or 100° C., or treating with acid (pH 3 to 4). The present invention analyzes DSW 2400 treated with ED procedures using commercial RENISHAW Raman spectrometer, the intensity of the deep sea water extract treated with autoclave for a 1,000 $cm^{-1}$ (wavenumber region) molecular vibration is significantly reduced than the deep sea water extract without sterilized in an autoclave. 1,070 peak intensity in the group of exposure to air on the second day detected by ESI/MS show significantly reduced. However, 1,070 peak intensities in groups of reducing exposure to air, treating with $H_2$ for 30 sec or adding antioxidants such as quercetin and EGCG on the second day are still hold. 1,070 peak intensity in each group is significantly reduced on the ninth day, but the groups of adding antioxidants such as quercetin or EGCG show higher 1,070 peak intensity.

Figure 10A:
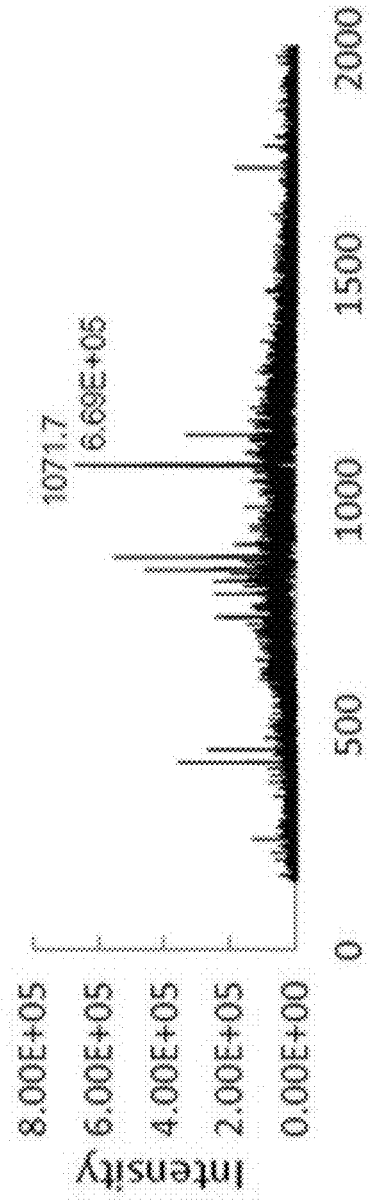
FIG. 10A shows the active components in DSW 2400 of the present invention.
Figure 10B:
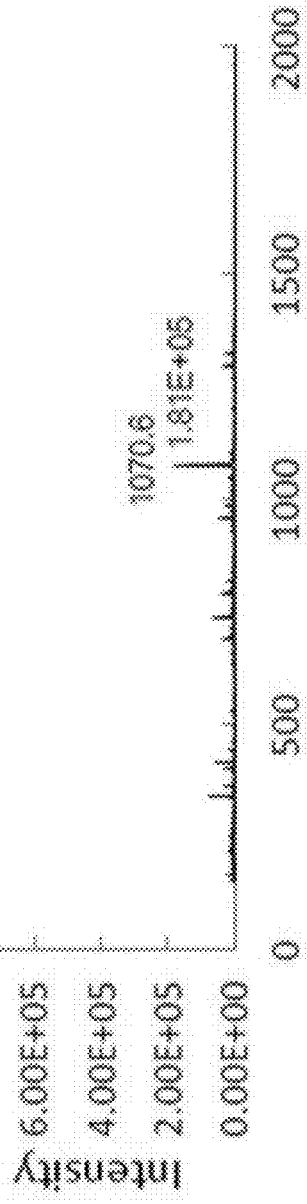
FIG. 10B shows that the antioxidant vitamin C destroys the active components in DSW 2400 of the present invention.

Additionally, the present invention is also used other antioxidants to compare with, as shown in FIGS. 10A and 10B, the antioxidant vitamin C destroys the active components in the DSW extract, which indicates that not all antioxidants can slow down the oxidation of the DSW extract.

EXAMPLE 7

Effect of the Deep Sea Water Extract on Inhibiting *Helicobacter pylori* Growth

Figure 11A:
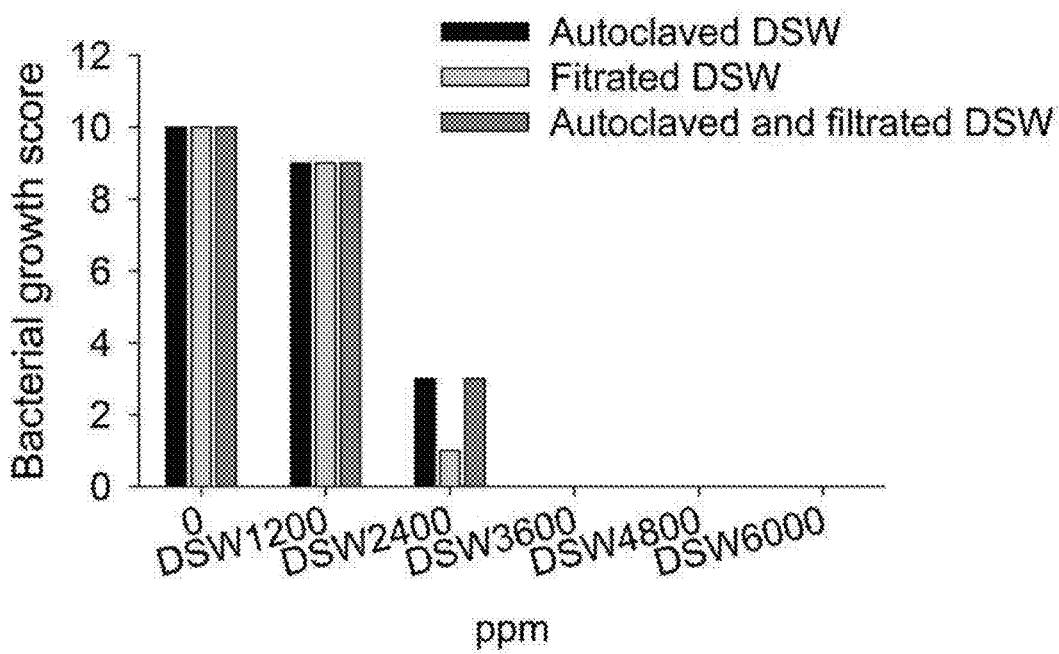
FIGS. 11A and 11B show that the DSW extract of the present invention has the ability of inhibiting *Helicobacter pylori* growth.
Figure 11B:
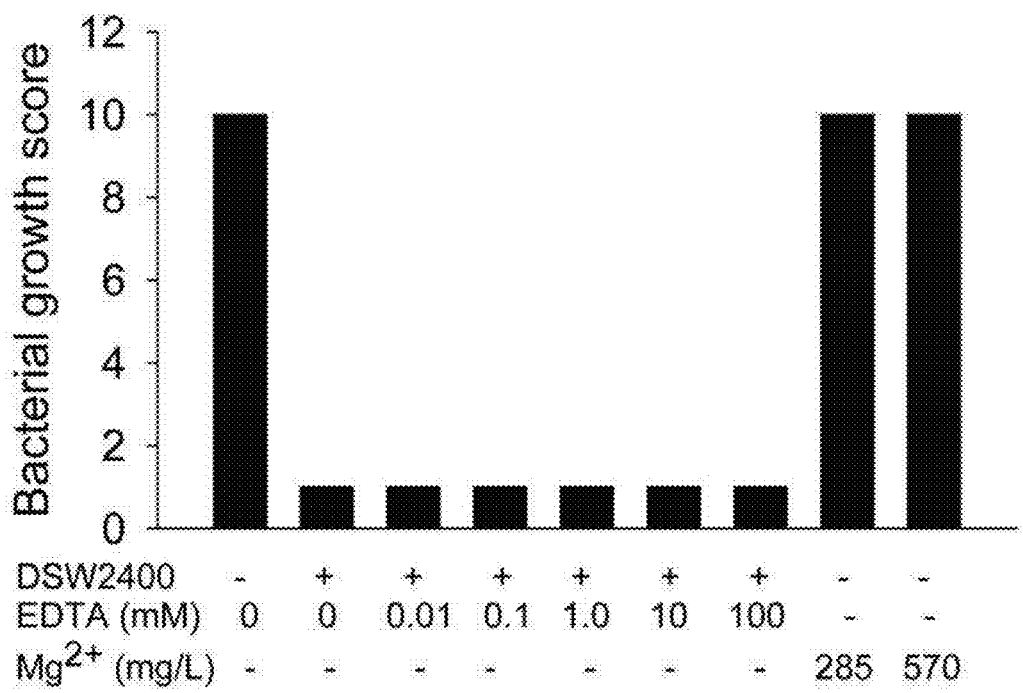

The present invention validates that the active components of the deep sea water extract having ability of inhibiting *H. pylori* growth are not associated with high magnesium, calcium ions and high hardness. As shown in FIG. 11A, the DSW extract with a hardness of 1,200, 2,400, 3,600, 4,800 and 6,000 ppm respectively are sterilized in an autoclave, 0.22 μm filter membrane and the combination of sterilizing in an autoclave and 0.22 μm filter membrane, which shows the DSW extract with hardness above 2,400 has the ability of inhibiting *H. pylori* growth, and the DSW extract treated with 0.22 μm filter membrane has better inhibition (FIG. 11A). The metal chelator EDTA of divalent cations is added to remove calcium and magnesium, the result shows that the DSW of the present invention does not contain calcium and magnesium ions, it still has the ability of inhibiting *H. pylori* growth. Therefore, the present invention also validates that the same concentration of magnesium ions does not have the ability of inhibiting *H. pylori* growth (FIG. 11B).

Figure 12D:
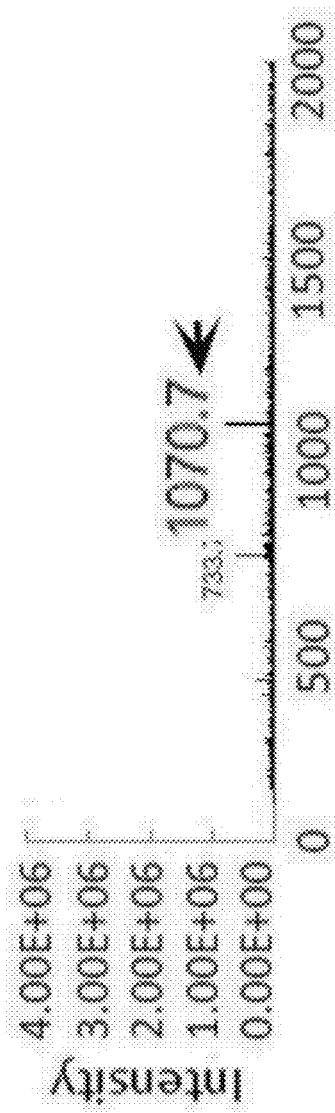
FIG. 12D is the intensity value of the 1,070 component of DSW 2400 at pH 3.93.
Figure 12E:
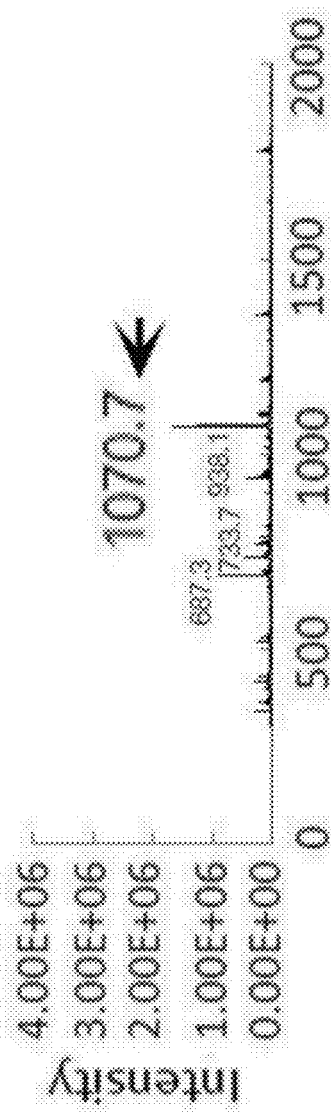
FIG. 12E is the intensity value of the 1,070 component of DSW 2400 filtered through a 0.22 μm filter membrane.
Figure 12F:
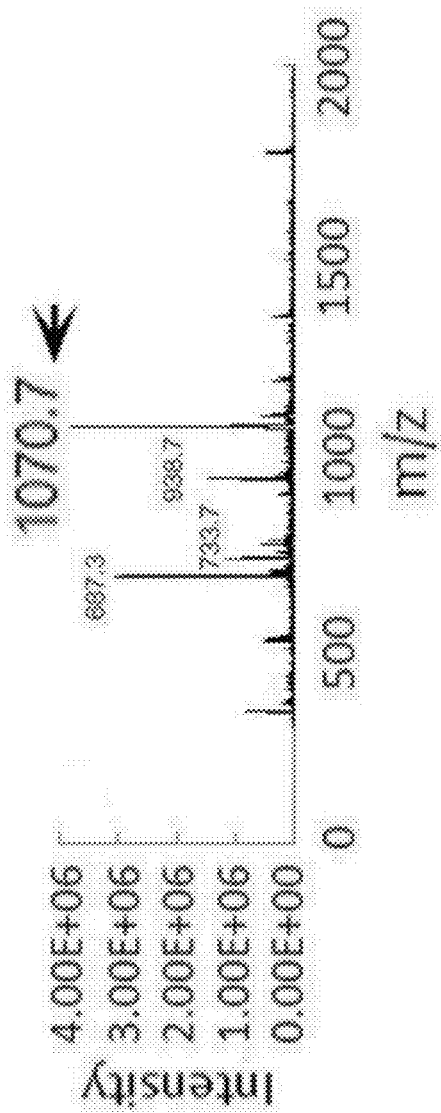
FIG. 12F is the intensity value of the 1,070 component of DSW 2400 treated with ED procedures.
Figure 12G:
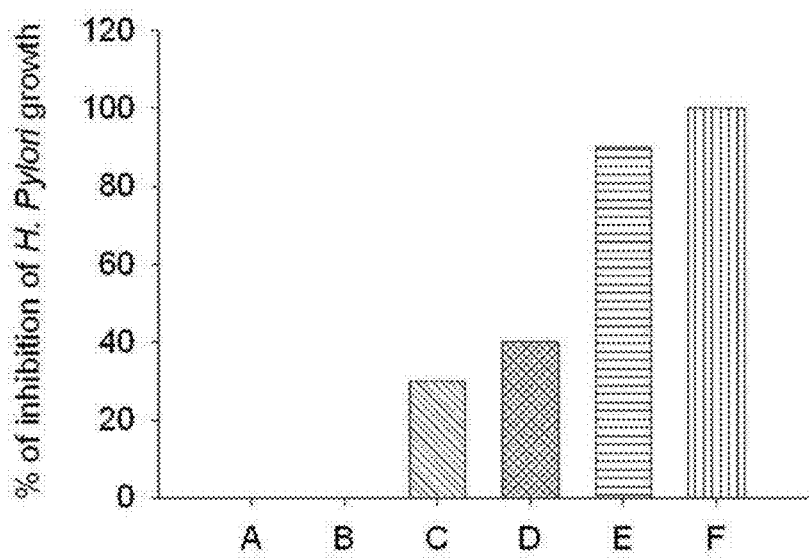
FIG. 12G is a relational graph between the intensity value of the 1,070 components of the DSW extract from FIG. 12A to FIG. 12F and inhibiting *H. pylori* growth rate. There is a positive correlation between 1,070 peak intensity of the DSW extract and the ability of inhibit *H. pylori* growth.
Figure 12H:
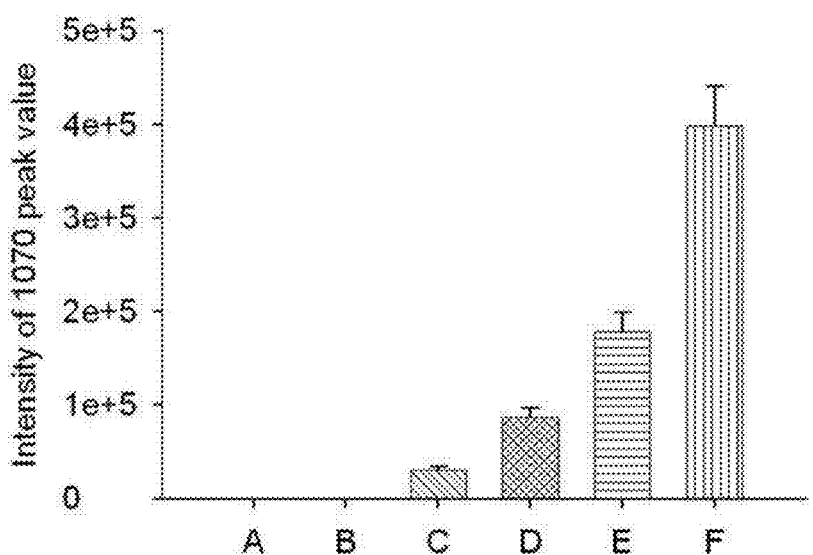
FIG. 12H shows the intensity values of the 1,070 components of the DSW extract from FIG. 12A to FIG. 12F.

Also, the present invention uses mass spectrometry to show a relational graph between the intensity value of the 1,070 component of the DSW extract and inhibiting *H. pylori* growth rate. In one embodiment, prepare the LB agar having the DSW extract with different hardness, the DSW extract with different concentration of EDTA or different concentration of $MgCl_2$, follow by filtration through the 0.22 μm filter membrane or sterilization in an autoclave. Mix the LB agar with sheep blood, and pour the mixture into each 9-cm culture plate. Let each plate cool until its solid to form agar plate. For the LB agar having different concentration of $MgCl_2$, take 2.85 mg $MgCl_2$, add other nutrients and water to make 10 mL agar plate, the agar plate contains 285 mg/L $MgCl_2$. According to above-mentioned procedure, the agar plats having different concentration of $MgCl_2$ are 285 mg/L and 570 mg/L. The present invention also prepares the LB agar having the DSW extract with 1,200 ppm to 6,000 ppm and the 2,400 ppm DSW extract with different concentration of EDTA. The present invention identifies the active components of the DSW extract having the ability of inhibiting *H. pylori* growth. The present invention collects ten *H. pylori* samples from different patients, and uses sterile cotton-tipped swabs to swab an appropriate amount of *H. pylori* transferring *H. pylori* to agar plate. The agar plate is then incubated in an anaerobic incubator for 3 to 4 days. After 3 to 4 days, the present invention observes whether there is any *H. pylori* growth, no *H. pylori* growth is indicated by −, a few *H. pylori* growth is indicated by +/−, and a normal *H. pylori* growth is indicated by +. As shown in FIG. 12, the higher concentration of DSW shows more effective ability of inhibiting *H. pylori* growth. The autoclave process can reduce the 1,070 peak intensity, but filtering through a 0.22 μm filter membrane do not affect 0.22 μm filter membrane, which indicates that 1,070 organic component of the DSW extract is the major component to inhibit *H. pylori* growth. FIG. 12G shows a relational graph between the intensity value of the 1,070 component of the DSW extract and inhibiting *H. pylori* growth rate. There is a positive correlation between 1,070 peak intensity of the DSW extract from FIG. 12A to FIG. 12F and the ability of inhibit *H. pylori* growth. FIG. 12A is RO water; FIG. 12B is surface of the sea (SSW, which is obtained at depth of 50 m under the surface of the sea); FIG. 12C is DSW 2400 sterilized in an autoclave; FIG. 12D is DSW 2400 at pH 3.93; FIG. 12E is DSW 2400 filtered through a 0.22 μm filter membrane; FIG. 12F is DSW 2400 treated with ED procedures; FIG. 12H shows the intensity values of the 1,070 components of the DSW extract from FIG. 12A to FIG. 12F.

Furthermore, another embodiment of the present invention is proceeded by a prospective, double-blind experiment, that is used to determine if the DSW of the present invention can significantly reduce $^{13}C$ urea breath value released from *H. pylori* infection or not.

First, the participants are male or female above 20 years of age having a gastroscopy due to abdominal pain or indigestion symptoms. They have chronic gastritis, mild erosive gastritis (diameter less than 5 mm, the number not exceed 3) or the scar stage of peptic ulcer, and also infected by *H. pylori*. They volunteer for this experiment, but they having one of following condition are excluded: 1) pregnant or breast-feeding women; 2) having other server disease such as kidney failure and liver cirrhosis; 3) incurable cancer; 4) severe bleeding ulcer; 5) post-gastrectomy patient; 6) taking bismuth salt, PPIs, antibiotics or nonsteroidal anti-inflammatory agents (NSAIDs) within a month before the gastroscopy. All the participants perform $^{13}C$ urea breath test ($^{13}C$-UBT) before performing gastroscopy and other diagnostic tests to determine the presence of *H. pylori* infection. After being introduced to the procedure, all the participants are asked to write informed consent. The routine health screening: complete blood count (CBC), liver function test (LFT), renal function test (RFT), blood glucose, blood lipid and electrolytes is carried out before and after treatment according to the procedure. $^{13}C$-UBT is performed before treating with the DSW extract, after treating with the DSW extract for 2 weeks and 4 weeks. The participants drink 200 mL the DSW extract or commercial mineral water (CMW) having the same drinking packages forth a day for 4 weeks (1 hour before meals and at bedtime). Meanwhile, the participants take prokinetics (metoclopramide 5-mg/tablet) three times a day to improve gastrointestinal motility, antacid (Stocain (oxethazaine 5 mg and polymigel 244 mg/tablet)) three times a day to relieve symptoms of indigestion after three males. During the treatment, all participates are asked to fill out the questionnaires recording the clinical symptoms and DSW extract drinking amount. The participates continue with their normal diet and usual drinks, but need to avoid following food or medicine: dairy products, Chinese herbs, honey, cranberry, health food containing lactic acid bacteria, excessive spicy and sour food etc. After the treatment of DSW extract, the participants are arranged an outpatient department to assess the compliance, event, level and frequency of adverse reaction, changing the number of *H. pylori* for a follow-up evaluation. Before the treatment of DSW extract, when (1) positive histological stains and $^{13}C$-UBT; or (2) positive bacterial culture is determined the presence of *H. pylori*. A change in $^{13}C$-UBT is as the basis for determining the effect of treatment.

Figure 13:
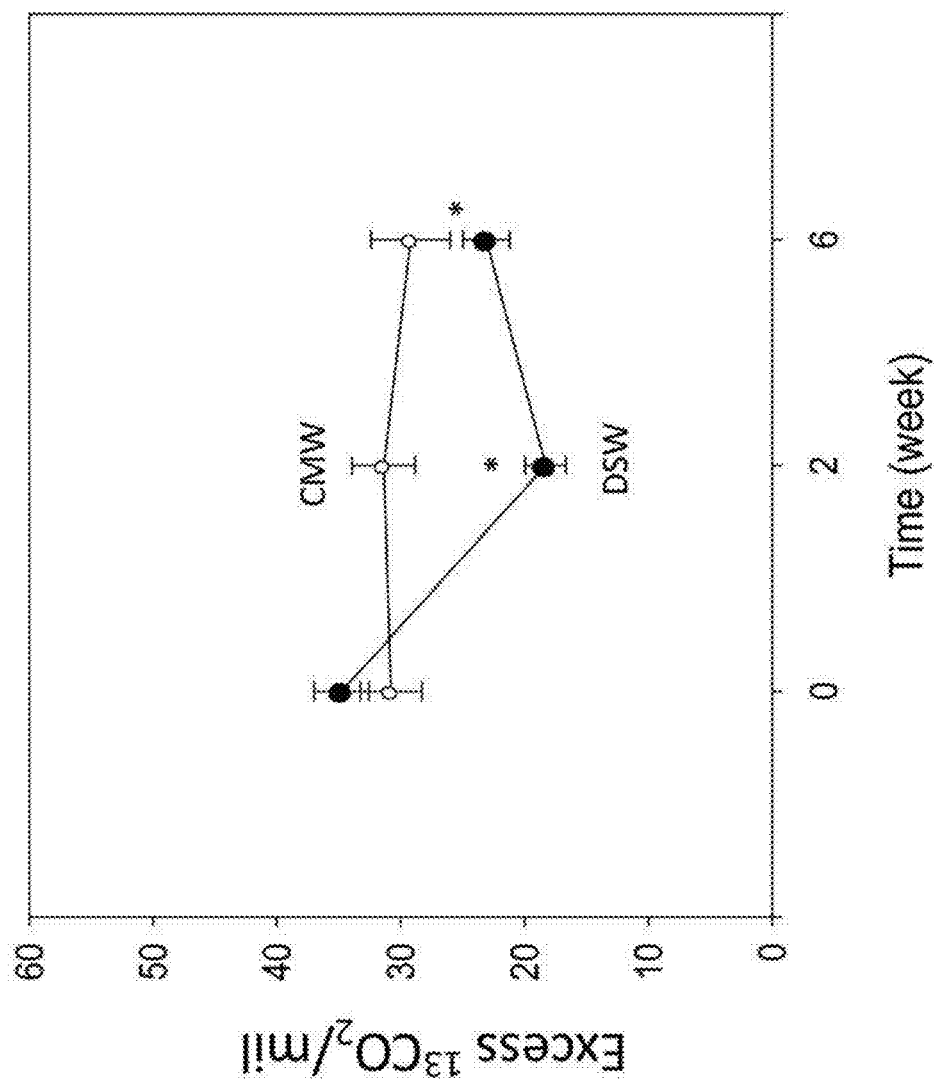
FIG. 13 is a curve diagram of significantly reducing $^{13}$C urea breath values released from *H. pylori* infection after the treatment of the DSW extract; DSW is indicated the DSW extract of the present invention, CMW is indicated commercial mineral water.

As shown in FIG. 13, the clinical data shows that the patient with positive *H. pylori* infection administrated the DSW extract containing 1,070 component can significantly reduce $^{13}C$ urea breath values released from *H. pylori* infection, and the CMW without 1,070 component cannot improve $^{13}C$ urea breath values and level of *H. pylori* infection.

The present invention provides a deep sea water extract containing an organic component with a molecular weight below 2,000, which can effectively inhibit *Helicobacter pylori* growth and use to be a new strategy for the treatment of *H. pylori* infection.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A method of inhibiting *Helicobacter pylori* infection, comprising administering an effective amount of a deep sea water extract to a subject in need thereof, wherein the deep sea water extract is obtained from a sea water under the surface of the sea by a filtration step of reverse osmosis (RO) and electrodialysis (ED) and an extraction step selected from the group consisting of dichloromethane (DCM) extraction, acetone extraction, chloroform extraction and combinations thereof;
    wherein the hardness of the deep sea water extract is 3,600 ppm to 6,000 ppm, Ca/Mg ratio of the deep sea water extract is 0.18; and
    wherein the deep sea water extract is treated in the presence of $H_2$ for 30 minutes.

2. The method according to claim 1, wherein the deep sea water extract is obtained from pasteurization or sterile filtration.

* * * * *